(12) United States Patent
Kalra et al.

(10) Patent No.: US 6,495,106 B1
(45) Date of Patent: Dec. 17, 2002

(54) AUTOMATED STAINING APPARATUS

(75) Inventors: Krishan L. Kalra, Danville, CA (US); Jason Z. Zhang, Dublin, CA (US); Zhi-Weng Chang, San Leandro, CA (US); Jianghong Shui, San Jose, CA (US)

(73) Assignee: BioGenex Laboratories, San Ramon, CA (US)

( * ) Notice: Subject to any disclaimer, the term of this patent is extended or adjusted under 35 U.S.C. 154(b) by 0 days.

(21) Appl. No.: 09/646,695

(22) PCT Filed: Mar. 24, 1998

(86) PCT No.: PCT/US98/05919

§ 371 (c)(1),
(2), (4) Date: Dec. 15, 2000

(87) PCT Pub. No.: WO99/49295

PCT Pub. Date: Sep. 30, 1999

(51) Int. Cl.[7] .......................... G01N 21/00; G01N 31/00; G01N 33/00; G01N 35/00; G01N 35/08; G01N 1/00; G01N 1/10; B01L 3/02; B01L 3/00; B05C 11/02; B05C 15/00; B05C 5/00; B05B 7/00

(52) U.S. Cl. ........................ 422/100; 422/99; 422/63; 422/67; 436/46; 436/54; 436/174; 436/180; 73/864.01; 118/120; 118/300

(58) Field of Search .............................. 422/63, 65, 67, 422/99, 104, 100; 436/46, 54, 63, 174, 180; 73/864.01; 118/58, 59, 300, 100, 120; 427/4

(56) References Cited

U.S. PATENT DOCUMENTS

| 5,854,075 | A | * | 12/1998 | Levine et al. ................ 118/100 |
| 5,879,628 | A | * | 3/1999 | Ridgeway et al. ..... 235/462.01 |
| 6,093,574 | A | * | 7/2000 | Druyor-Sanchez et al. . 422/100 |
| 6,096,271 | A | * | 8/2000 | Bogen et al. ................ 422/100 |
| 6,180,061 | B1 | * | 1/2001 | Bogen et al. ................ 219/385 |
| 6,181,811 | B1 | * | 1/2001 | Kuan et al. .................. 359/391 |
| 6,183,693 | B1 | * | 2/2001 | Bogene et al. ................. 422/64 |
| 6,258,322 | B1 | * | 7/2001 | Meikle ........................ 118/100 |
| 6,296,809 | B1 | * | 10/2001 | Richards et al. ............ 141/145 |
| 6,309,607 | B1 | * | 10/2001 | Johnston et al. ............ 118/423 |
| 2002/0072122 | A1 | * | 6/2002 | Copeland et al. ............. 436/46 |

* cited by examiner

Primary Examiner—Jill Warden
Assistant Examiner—Brian R. Gordon
(74) Attorney, Agent, or Firm—James C. Weseman, Esq.; The Law Offices of James C. Weseman

(57) ABSTRACT

Disclosed is an automated staining apparatus including an arm (30) moveable in three dimensions, and a hollow tip head (70) located on the arm including integral reagent tip head (40), wash tip (41) and blow tip (42) for selectively dispensing gas and liquid onto microscope slides. Also disclosed are various sub-components of the apparatus that are specifically adapted to the processing of specimens on slides.

24 Claims, 18 Drawing Sheets

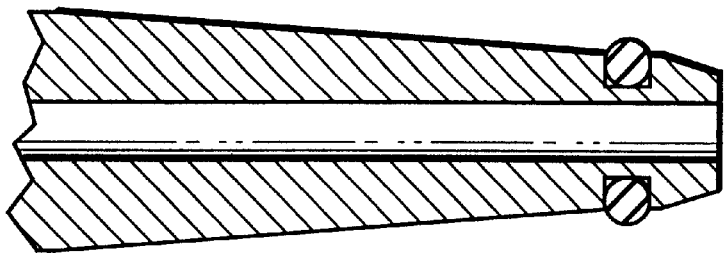
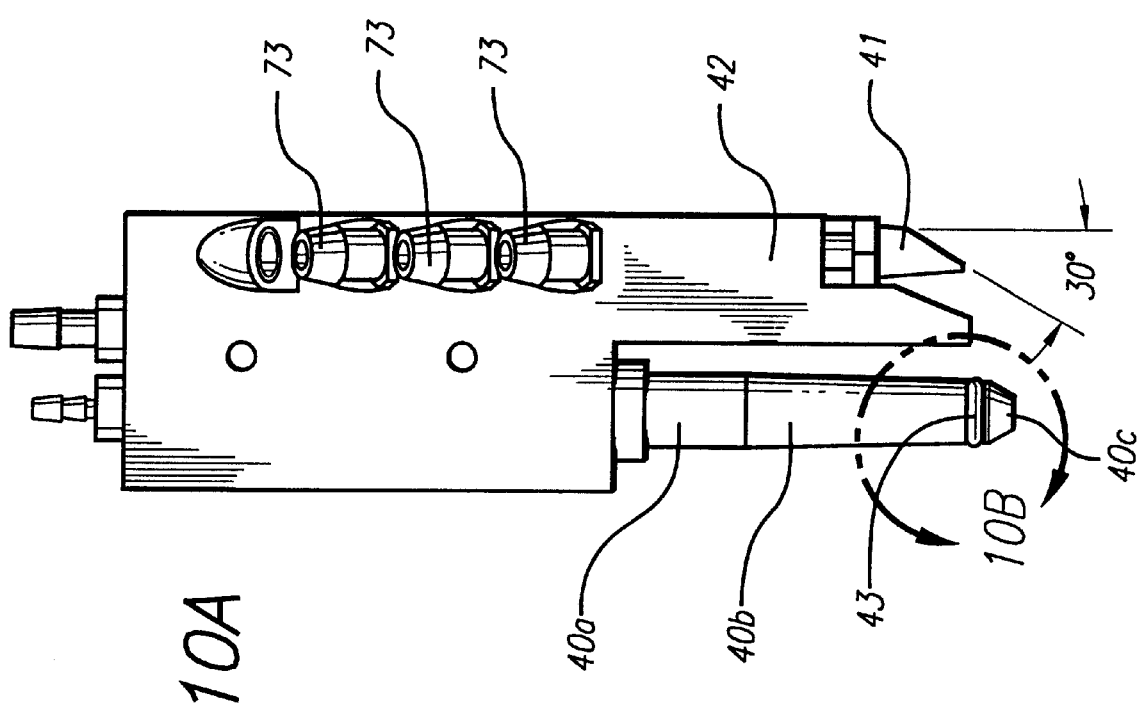

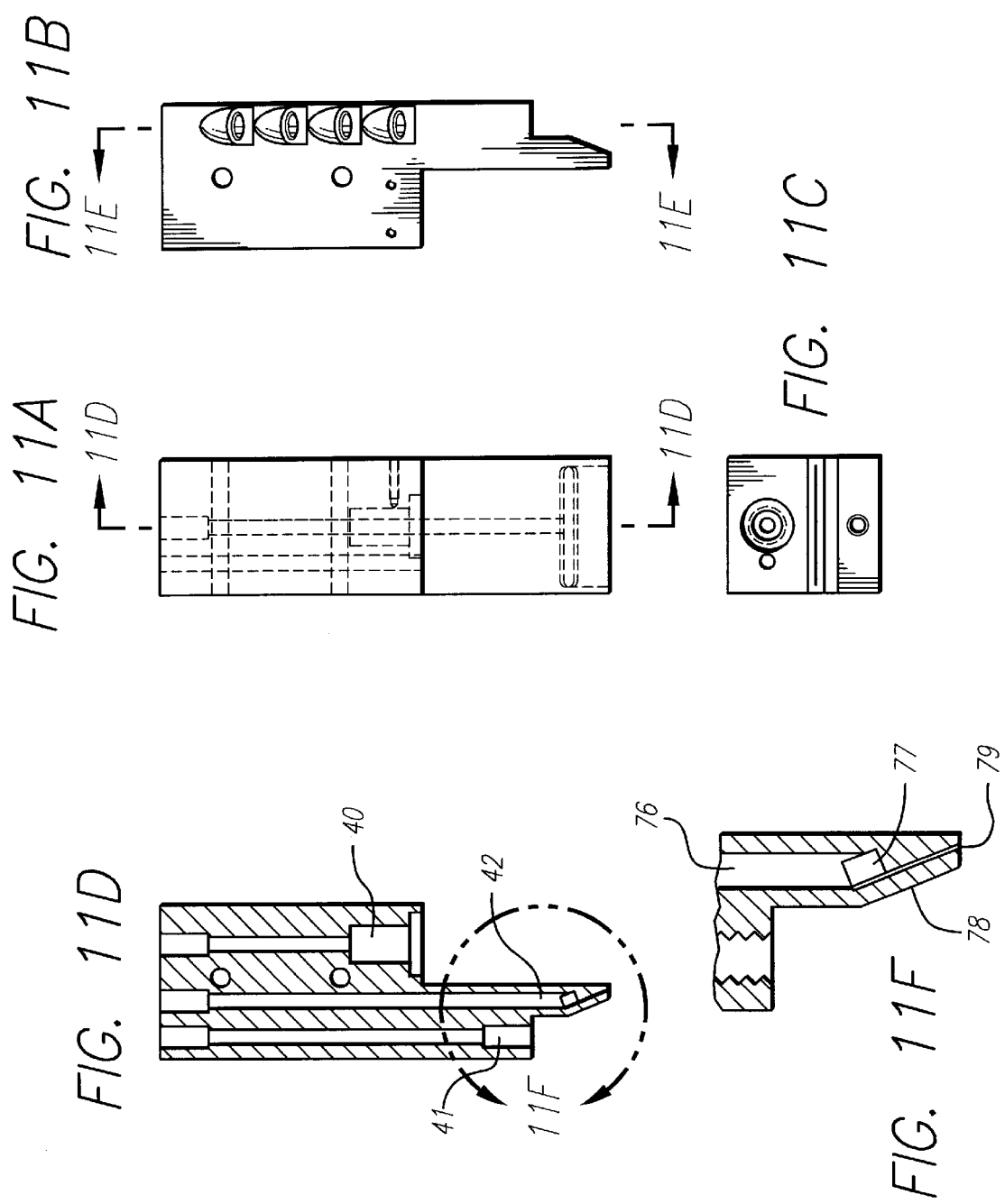

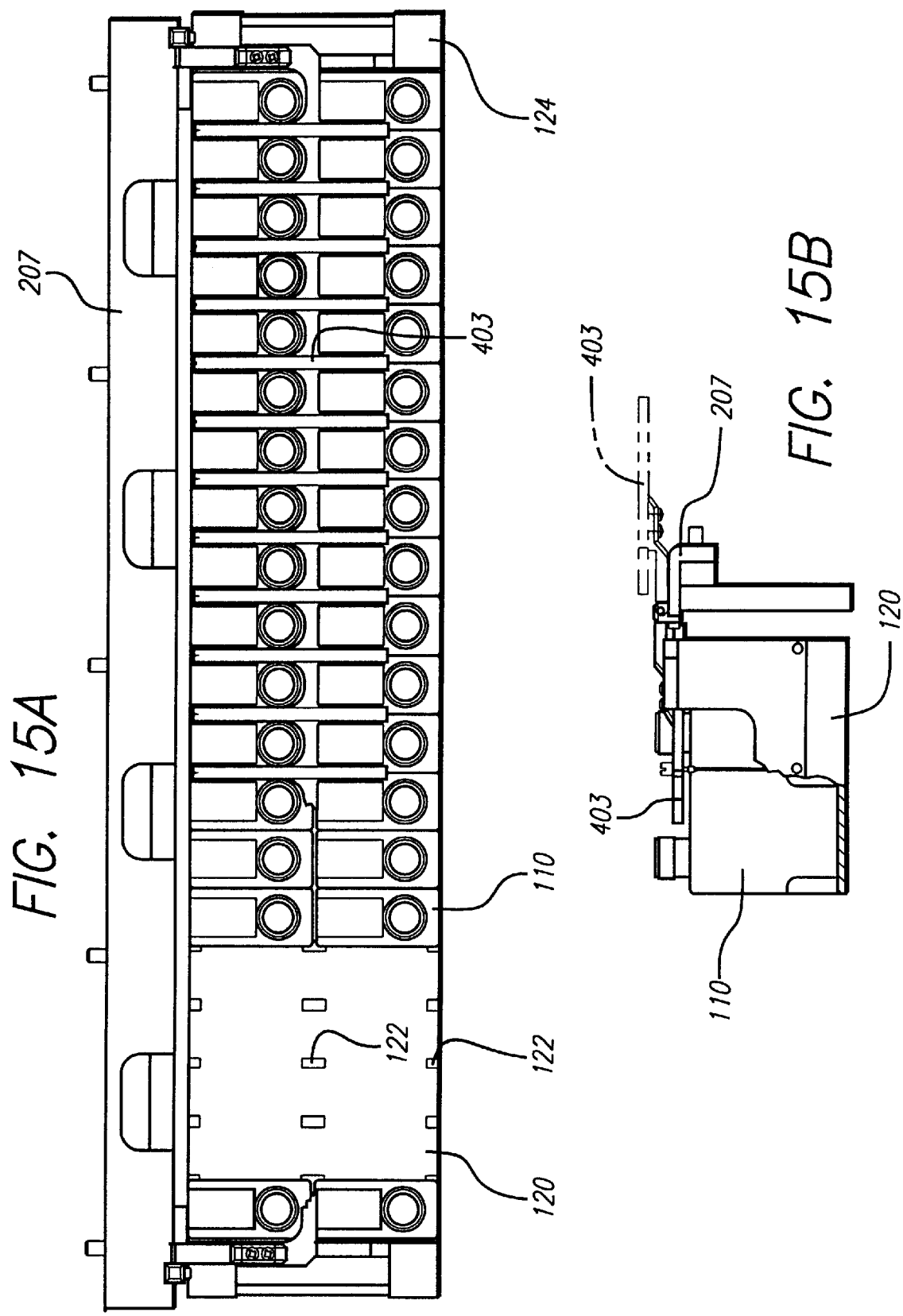

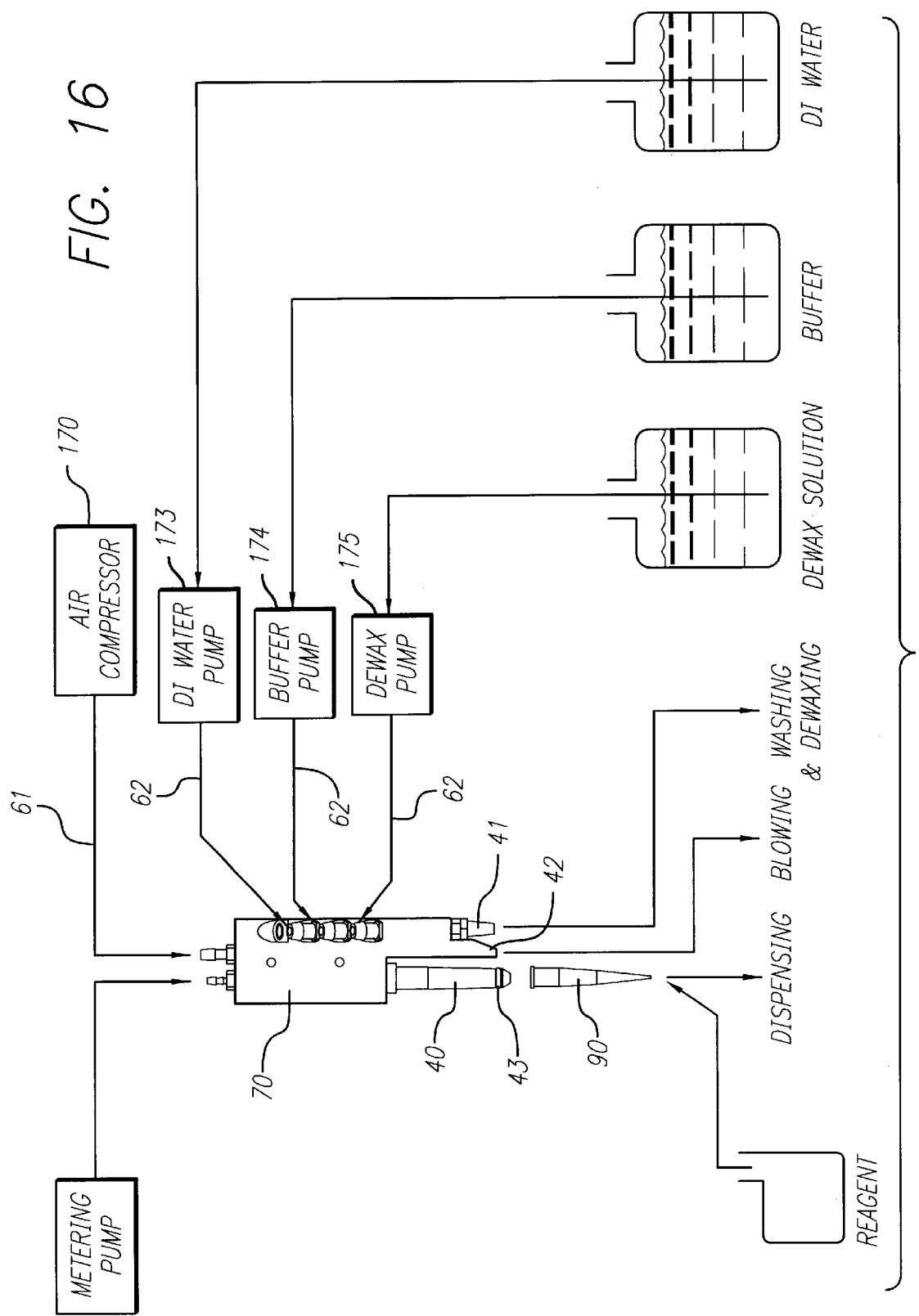

AUTOMATED STAINING APPARATUS

This is a national stage application of International Application No. PCT/US98/05919 filed Mar. 24, 1998.

TECHNICAL FIELD

The present invention relates to automated equipment used in the staining of cells and tissues on microscope slides.

BACKGROUND OF THE INVENTION

Microscopic examination of unstained cell and tissue specimens often suffers from a lack of contrast between individual cells and the background matrix or between individual parts of cells. In order to alleviate this difficulty, stains that are taken up differentially by cells or parts of cells have been used for over a century.

Because of the manner in which microscope slides with tissue specimens are prepared (see Elias, J., "Immunohistopathology: A practical Approach to Diagnosis" ASCO Press, 1990, pp. 3–4, for examples of such preparation), the size and/or location of a tissue specimen on a microscope slide can vary considerably within a relatively large area of the slide. In order to apply a stain to the correct location on a slide and to provide rinsing and other manipulation steps at appropriate times and in proper amounts, until recently all such staining operations were carried out by hand. However, modern laboratories that examine large numbers of tissue specimens find it desirable to automate the staining process. Accordingly, a number of manufacturers have developed equipment for automated staining of tissue specimens on slides.

For example, U.S. Pat. No. 4,985,206 describes an apparatus and process for automating the application of staining reagents to a thin tissue section mounted on a microscope slide. The apparatus and method use a channel-defining element that is assembled with the microscope slide to provide an enclosure of capillary dimensions into which liquids can be injected. Liquids are added sequentially to the capillary space, where the addition of a new liquid forces out the previous liquid. A plurality of these assemblies of microscope slides and specialized covers can be placed in a rack on an apparatus for automated addition of liquids.

A further automated immunostaining apparatus, known as the Ventana 320™ is produced by Ventana Medical Systems, Inc. This apparatus applies a liquid known as Liquid Coverslip™ to each slide prior to reagent addition. Liquid Coverslip™ is a non-aqueous material having a density less than that of water. When a reagent dissolved in water is added to a microscope slide, the reagent sinks to the bottom of the Liquid Coverslip™ layer, spreading across the surface of the slide. Slides are organized on a carousel which rotates beneath a dispensing head of the apparatus for application of reagents or wash fluids.

Yet another apparatus, known as the Jung Histostainer Ig™ Automated Immunostainer, is produced by Leica Instrument GmbH. This is also a carousel-type device, but reagents are applied by a spraying operation rather than by dropping liquid onto an organic film. The apparatus contains a permanent reagent spraying head that can be moved along a single axis to provide spray coverage over a microscope slide located on the rotating tray when the slide is rotated into position underneath the head. Excess reagent is removed by a permanent clearing nozzle which blows air in a pressure front across the slide, forcing excess liquid off at the completion of the reagent incubation step.

A further apparatus is the subject of U.S. Pat. No. 5,439,649. This device includes an arm moveable in three dimensions attached to a framework. A hollow tip head is carried on the arm, and includes a wash/blow head for dispensing reagents and clearing the slides. The reagent application tip can be attached to the hollow tip head or removed by a pre-selected movement of the arm.

All of these devices attempt to solve certain conflicting goals in automated apparatuses of this type. For example, it is desirable to minimize the use of expensive or toxic reagents, particularly reagents used in immunostaining (e.g. antibodies and other reagents of biological origin), while insuring complete coverage of the specimen on the microscope slide by the reagent. However, the penultimate-referenced spraying operation above uses an excess of reagent, which must then be removed in order to obtain satisfactory coverage. Other techniques require additional manipulative steps, such as the use of a hand-assembled cover or an additional liquid reagent to provide for proper spreading of the reagent. It is considered desirable to have an automated apparatus that can use regular microscope slides without additional manipulation and that does not require the use of either excess reagent or the use of an organic liquid with additional manipulation and disposal steps.

In addition, current automated equipment used in the staining of cells and tissues on microscope slides are limited in the functions they can perform, such as removing the wax or embedding medium surrounding the tissue specimen, and by concerns with cross-contamination between slides or between reagents.

Accordingly, further developments that allow individual slides to be treated differently in a single batch operation and that provide an automated procedure which uses reagents efficiently remain desirable.

Furthermore, it is also considered desirable to provide the capability of performing additional functions associated with tissue staining procedures in an automated device, without substantial risk of cross-contamination.

It is therefore an object of the invention to provide an automated staining apparatus that is readily programmable to allow automated staining of individual microscope slides with different techniques in a single operation without user intervention.

It is a further object of this invention to provide an automated staining apparatus that uses staining reagents efficiently with a minimum of waste and without extraneous steps.

It is a still further object of this invention to provide an automated staining apparatus that can perform additional preparation steps as part of a completely automated staining protocol.

It is also an object of this invention to provide an automated staining apparatus that minimizes the risk of cross-contamination between slides, reagents and solutions.

DISCLOSURE OF THE INVENTION

These and other objects of the invention have been attained by providing an automated staining apparatus, comprising a supporting framework, at least one arm moveable in three dimensions attached to the framework; a means for moving the arm, and at least one hollow tip head located on the arm. The hollow tip head will include at least one reagent tip head having a means for releasably engaging a pipette tip by a pre-selected movement of the arm and a means for alternatively supplying positive or negative gas pressure to the reagent tip head to withdraw or dispense volumes of liquid onto a microscope slide. The hollow tip head will also include at least one wash tip having a means for selectively dispensing a plurality of liquids onto the microscope slide and at least one blow tip having a means for selectively dispensing a gas onto the microscope slide via an exit slit substantially equal in length to the width of the slide. The apparatus will also include at least one pipette tip holder at a predetermined location on the framework adapted for holding a plurality of pipette tips adapted to be releasably attached to the reagent tip head, at least one reagent vial holder at a second predetermined location on the framework adapted for holding a plurality of reagent vials, and at least one microscope slide holder at a third predetermined location on the framework adapted to releasably contain the microscope slide. The apparatus will also include a control means operatively connected to the means for moving the arm, the means for alternatively supplying positive or negative gas pressure, the means for selectively dispensing a plurality of liquids, the means for selectively dispensing gas and the means for controlling movement of said arm between said predetermined locations. The control means will be adapted to cause the tip head to engage a pipette tip, to release the pipette tip, to withdraw a reagent from the reagent vial, to dispense the reagent onto the slide via the pipette tip, and to dispense a gas or a liquid onto the slide through the wash tip and the blow tip.

Other aspects of the present invention will be readily apparent from the following more detailed description.

BRIEF DESCRIPTION OF THE DRAWINGS

FIG. 10 depicts an embodiment as depicted generally in FIG. 9, and in detail depicts a cross section of a portion of the reagent tip head of the Z head;

FIG. 11 depicts multiple detailed views including elevations and cross sections of the wash tip and the blow tip portions of the Z head;

FIG. 15 depicts a top plan view and side elevation in partial cross section of a reagent vial holder of the invention;

FIG. 16 is a schematic view showing major components of the apparatus that supply gas and liquid to the Z head, along with an indication of an embodiment for the attachment of the supply conduits and other parts associated with the Z head and movable arm;

DETAILED DESCRIPTION OF THE INVENTION

Figure 1:
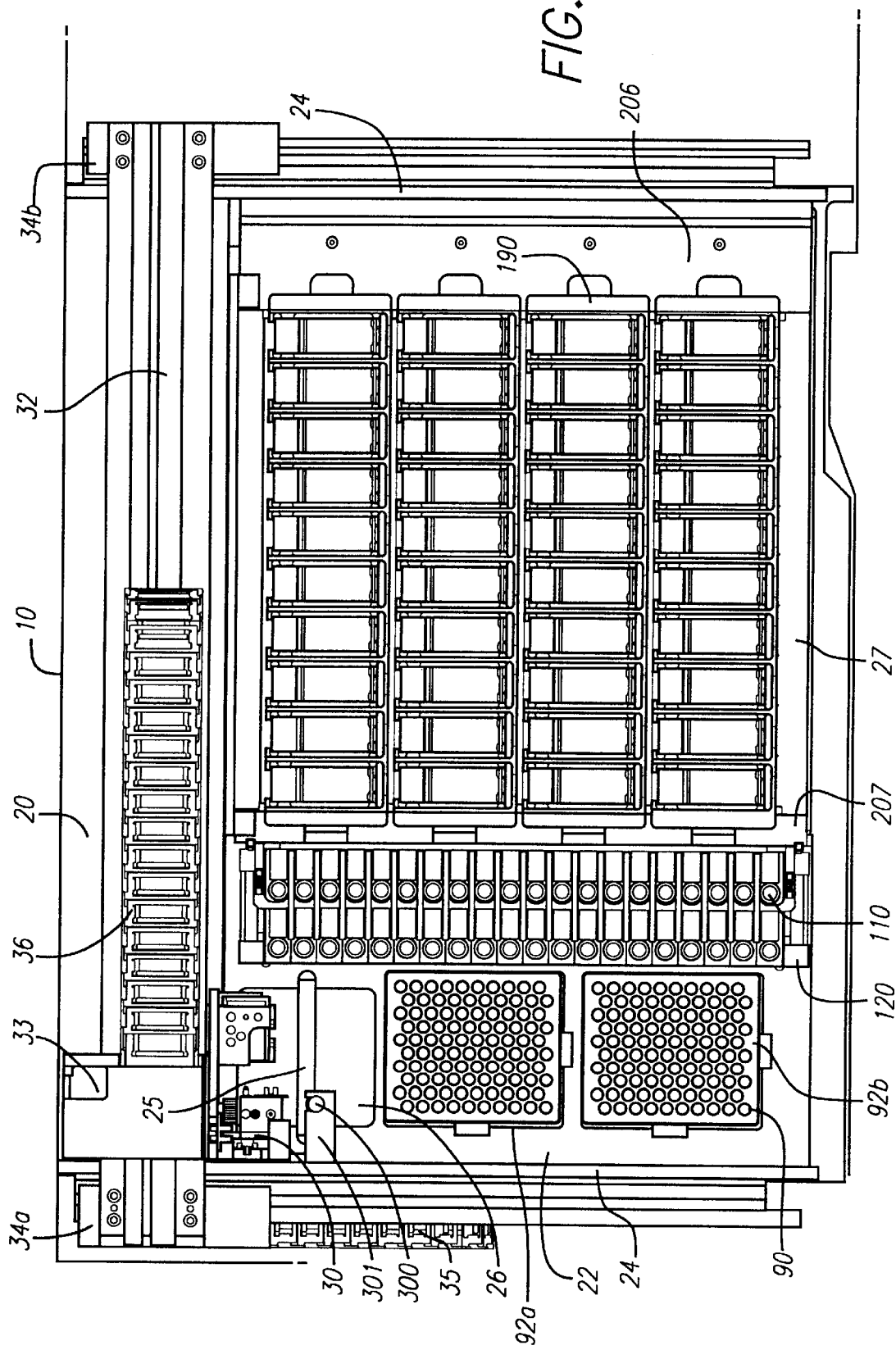
FIG. 1 is a top plan view of an embodiment of an apparatus of the invention (shown without a cover on the apparatus)

The present invention provides an automated apparatus for staining cell and tissue specimens on microscope slides, as well as various subsystems for use in the present apparatus and a variety of alternative devices. The apparatus will first be described generally along with its operation, after which the apparatus and various component parts will be described in detail with reference to the figures that form a part of this specification.

The apparatus of the invention comprises a supporting framework to which an arm movable in three dimensions is attached. Motors or other means for moving the arm are provided under the control of a computer or other electronic control device that allows programming of movement of the arm between various work locations on or within the framework. A hollow tip head is located on the arm so that liquids or gasses can be dispensed or withdrawn through the head to provide for the various work operations described below. In certain embodiments of the invention, the arm is configured so as to have either multiple, permanently attached tips with different functions or multiple disposable tips located on the arm at the same time. However, in preferred embodiments of the invention a single hollow tip head is provided having multiple channels connected to separate pumps to which individual tips having different functions will be attached. In a preferred embodiment, a portion of the hollow tip head is adapted to pick up disposable plastic pipette tips from the standard containers in which such tips are supplied (for example, Catalog No. 3510-R from E&K Scientific Products, Saratoga, Calif.). These disposable pipette tips are currently sold in a rack which presents the base of the tip for insertion of a hand-held pipette body into the hollow tip, the tips being arranged in an array so that all individual tips in the container are accessible to the user. As will be apparent from the description below, the same or similar standard racks of pipette tips can be used in the apparatus of the present invention.

One feature of the apparatus of the present invention is the integration of a blow tip and a wash tip in the hollow tip head (hereafter termed the "Z head" because it is the primary component of the present apparatus which moves in the 'Z' dimension). In the blow tip there will be an exit slit that is usually substantially equal in length to the width of a microscope slide. If the slit is not equal to the width of a microscope slide with which it is intended to be used, it is preferred that the slit be slightly wider than the microscope slide. A narrower slit is less efficient in removing liquid from the microscope slide surface in the manner as described below. However, the practical width of the slit is limited by the desire to have a number of microscope slides arranged together in close proximity in the apparatus of the invention and further to avoid wasting buffer or other wash solutions that are applied to a slide through the tip. In the blowing operation that removes excess wash/buffer solution, the exit slit on the blow tip provides a "wall" of gas, typically air, that pushes excess liquid from the surface of a microscope slide as the tip is passed over and parallel to the slide (described below in greater detail). The wash tip is a separate orifice located in close proximity to the blow tip, and is used to deliver diverse liquid solutions to the slide.

The framework of the apparatus is also provided with holders at predetermined locations for reagent application tips (hereafter termed pipette tips), among other removable items. Thus, programming of the arm to move to a particular predetermined location and carry out a pre-selected motion or other operation discussed herein allows the individual tips to be placed onto or released from the hollow tip head. A holder for a reagent container, more typically a plurality of reagent vials (each reagent vial containing, for example, a stain or any of various solutions associated with staining) and a microscope slide holder are also present on the framework at other predetermined locations. Thus, standardized motions of the arm can be programmed into the control unit so that individual microscope slides at specific predetermined locations in the microscope slide holder can be treated with reagents and/or wash fluids obtained from reagent vials or from liquids supplied through the hollow tip head on the movable arm. In addition, the attachment steps (and optionally the detachment step) for attaching pipette tips to the Z head on the moving arm can be carried out by a pre-selected movement of the arm, much in the same manner that disposable pipette tips are now pressed onto and later removed from the end of a hand-operated pipette.

In a typical operation of the apparatus of the invention, multiple slides, each typically having a tissue specimen at some location on its upper surface, are placed horizontally in a tray that is inserted into the apparatus at a predetermined location, usually at a location having registration pins that fit into registration holes in the tray or similar registration means) so that the individual microscope slides are always located in the predetermined relative positions on the frame of the apparatus. The apparatus is programmed as appropriate for the individual slides being treated and reagent vials are placed at their own predetermined locations in the apparatus in the same manner as the tray described above. Likewise, pipette tips are also made available for engagement and use by the moveable arm. For example, a standard rack of 1 mL pipette tips can be placed at its predetermined location in the apparatus.

Once all components are in place, the apparatus carries out all preparation, reagent application, incubation, heating (if necessary or appropriate), and specimen rinsing steps to perform the desired staining operation. In a typical operating sequence, the Z head on the movable arm moves to each of the slides being treated in a particular cycle and begins by applying the liquid from the wash buffer reservoir via a liquid supply conduit to the wash tip of the hollow tip head. The apparatus will then use the blow tip to remove excess buffer from the slide prior to reagent delivery. This removal is accomplished by blowing gas through the blow tip while the head travels along the length of the slide; a 'wall' of gas exits the slit and removes excess buffer from the slide, without disrupting the tissue specimen. A small amount of buffer desirably remains on the slide to assist in reagent distribution.

The Z head on the movable arm then engages a disposable pipette tip from the pipette tip rack that has been inserted into the pipette tip holder in the apparatus. The Z head with the pipette tip attached then takes up a reagent to be applied to a slide or group of slides from a reagent vial in the reagent container holder. For efficiency, a number of slides can be treated with a single reagent at the same time. The reagent is dispensed on the slide in a pre-assigned pattern that operates in combination with the thin liquid film on the microscope slide to assure spreading of the reagent over the entire surface of the slide to which the tissue specimen is attached. The thin liquid film allows less reagent to be used than would be required if the film were not present to assist reagent distribution.

The disposable pipette tip is then discarded, and the movable arm moves the Z head wash and blow tips to the microscope slide to apply buffer and then remove excess buffer from the next group of slides to be processed, while the prior group of slides are being incubated with the reagent. The movable arm then engages the next available disposable tip from the tip rack, and the appropriate reagent is drawn into the tip and applied as before. Appropriate steps are repeated until all slides have been treated with reagent or until a reagent incubation is complete, so that reagents may then be removed from the appropriate slides.

Once a reagent incubation is complete, the slides are rinsed when the movable arm moves the wash and blow tips to the microscope slide again, and buffer is applied to the slide to rinse off the majority of the reagent. The blow tip then removes the excess buffer from the slide, and the slide is rinsed a second time with the on-line buffer, if desired. This procedure of rinsing and removing excess buffer from a slide is repeated as desired, depending upon the individual stain and the appropriate procedure for rinsing the reagent. The control mechanism, generally a programmable computer, keeps track of the time of the various incubations and repeats the steps above as appropriate in order to apply the appropriate reagent to all of the slides that have been inserted into the tray.

One feature of the apparatus of the invention that allows efficient use of reagents is the method of spreading reagents described above and further described in detail below. When a standard liquid staining reagent is dropped onto a glass slide, the reagent tends to stay in the location where placed, rather than spreading over the entire surface area of the slide. Since the location of the tissue specimen on a slide is variable, and may not be located in the same place from one slide to the next, automated procedures previously required that the reagent be applied over the entire surface area of the slide. While this could be accomplished by applying a relatively large amount of a dilute reagent, many staining operations do not permit the use of dilute reagents, and some stains are sufficiently expensive so that applying concentrated reagent over the entire slide, including areas where no tissue is present, would be a major cost of operation. Accordingly, a special application system has been devised for use in the apparatus of the present invention; this system can be used generally in the manner described here for other automated equipment.

The slide to which a stain reagent will be added is first washed with an aqueous wash solution, usually a buffer, that contains one or more surfactants which reduce the surface tension of water. However, it is not deemed entirely satisfactory merely to flood a slide with an aqueous solution of surfactant, since a concentrated reagent added to the slide will then be diluted on the slide. Accordingly, the blow tip of the invention is designed so that excess buffer can be removed from the washed slides to produce a thin film of the aqueous solution. The height of the blow tip exit slit above the microscope slide, the pressure of the compressed gas being blown through the tip, and the rate of movement of the tip are selected to allow a controlled amount of buffer to remain on the slide. If too much buffer remains, the reagents will be diluted as discussed above and will not work optimally. If too little buffer remains, the buffer may evaporate prior to reagent application, and the reagents will not spread sufficiently. Specific techniques for controlling the parameters of the wash tip and blow tip operation to select the desired amount of buffer are described below.

In addition to the buffer and use of the wash tip and blow tip as described above, the invention also provides for dispensing of reagents on the slide in a pattern that assists spreading. A pattern is selected so that a reagent is not required to diffuse for great distances through the surface film; for example, convoluted application patterns can be selected so that the reagent need not diffuse more than one-fourth (or some other fraction) of the width of the microscope slide. The combination of the buffer film and the application pattern (typically dropwise or in a stream) ensures adequate coverage of the slide regardless of the location of the tissue and allows less reagent to be used than would be required in the absence of a surface film. In a typical operation, the amount of reagent added is less than that which would be required to cover the slide if no aqueous film were present on the slide.

In addition to these general operations and components of the invention, the apparatus of the invention can contain additional subsystems for convenience, such as drain pans, reagent vials and other components that are described below in more detail.

Another feature of the apparatus of the invention is the system control format and method. The apparatus provides two control formats to control the staining process parameters: 'Open' format and 'closed' format. The 'open' format provides great flexibility for the user of the apparatus. In this format, the system allows the user to create, change, and adjust numerous system settings, running parameters and staining protocols in the processing of individual tissue specimens on microscope slides to meet different requirements. On the other hand, in the 'closed' format, the system maximizes the process automation and very little user input is needed. It is especially useful for those users who utilize large batch quantity and similar processing procedures. A bar-code technology can be used in this format. On the upper surface of each reagent vial, there will be a label affixed at a predetermined location when it is shipped. Three bar-codes are printed in close proximity to each other on the label. The information content of the bar-code can include: 1) Name of the reagent solution; 2) Manufacture date; 3) Expiration date; 4) Serial number; 5) Reagent volume. A human-readable string is also printed on the label and is shown on the side wall of the reagent vial. In addition, there will be a pre-printed label applied to a region on the upper surface of the microscope slide. This label is intended for the user to include certain information. The content of this bar-code will include the name of the protocol to be used in processing the particular slide. A human-readable string can also be printed immediately under this bar-code as well. The height of the bar-code is generally approximately 0.25 inch, so that there will remain sufficient space for the user to write any other desired information. The coding used in this application will desirably be code 128, as this code can provide advantageous information density.

Before initiating an operation, the apparatus moves a laser bar-code scanner around the bar-codes located both on the microscope slides and the reagent vials. The digital computer will then recognize the reagents and the slides to be treated, and will calculate the required volumes of the reagents. A reagent map can also be printed by the computer for user reference. If any deficiency occurs in the reagent supply, the computer will halt the processing and request additional reagent supplies. At the same time, if any unknown protocol is detected, the computer will request that the user create a new one. After this verification, the computer will control the apparatus as discussed above to automatically process the staining operations.

The invention now being generally described, the same will be described in reference to the figures, using the same reference numbers throughout to represent either identical parts that appear in different views of the same embodiment or parts in different embodiments that have identical functions.

FIG. 1 depicts an embodiment of the invention in plan view from above. In order to make visible the movable arm and other working parts of the apparatus, the apparatus of FIG. 1 is illustrated without a cover such as would normally form the upper surface of the apparatus and act in concert with retaining walls to enclose the working parts and microscope slides. In this view, the front of apparatus 10 is at the bottom of the figure.

In this view, movable arm 30, which will carry out numerous operations of the apparatus, is visible in its home position in the rear-left corner of the interior of framework 20 which forms the cabinet surrounding the working parts of apparatus 10 (upper-left portion of FIG. 1). Framework 20 is formed from various components, such as baseplate 22 and side plate 24, that form the cabinet. The various locations and the corresponding parts of the apparatus or materials that are inserted into the apparatus at these locations are generally visible on baseplate 22. Beneath and slightly in front of the movable arm home position is a square shaped tip disposal orifice 26. A tip disposal bin 28, used for holding discarded pipette tips 90 (described below), is located under the baseplate 22 and is desirably designed as a drawer so that it can be withdrawn from the front of the apparatus 10 (see FIG. 2). A horizontal bar 25 is located at the center of the tip disposal orifice 26 and is used to prevent discarded pipette tips from stacking up and blocking the disposal orifice. Under the slide tray 190, there is a drain bin 27, which can simply be a container provided with a drain line to a waste container. These and other parts of the apparatus are generally adapted to be retained in a specific location on baseplate 22 by providing matching projections and depressions, or some other means for locating the indicated part of the apparatus on the base plate at a predetermined location.

Immediately in front of tip disposal orifice 26 in this first embodiment is the predetermined location for pipette tip holder 100 (not visible in this view). In this embodiment, holder 100 is adapted to retain in position two standard pipette tip racks 92a and 92b each containing arrays of disposable pipette tips 90. One example of an appropriate holder 100 for pipette tips 90 (actually for tip racks 92a and 92b) are raised regions on baseplate 22 around which the bases of pipette tip racks 92a and 92b fit snugly.

To the right of pipette tip racks 92a and 92b is a reagent vial holder 120, in this embodiment in the form of a reagent vial rack. The reagent vial holder 120 can either be affixed to the baseplate 22 or, in the manner described above, it can be adapted to be removable from the baseplate for loading with reagent vials 110 in a more convenient location. The reagent vial holder 120 is adapted to be retained by the baseplate in a predetermined location and orientation, so that any given reagent vial 110 will always be in the same relative position on baseplate 22.

To the right of reagent vial holder 120 is the microscope slide holder, in this embodiment occupied by four 10-well microscope slide trays 190. Each tray 190 is retained in a predetermined location and orientation relative to baseplate 22 and the remainder of the framework 20, so that each microscope slide 130 retained in a well is in a predetermined location relative to the baseplate 22.

Movable arm 30 is transported to different locations over baseplate 22 by the action of various motors that operate in combination with sliding tracks to precisely position the movable arm 30 at its desired location within framework 20, in order to carry out the operations described herein. Visible in FIG. 1 (at the top of the figure) is the X-axis track 32, in this embodiment the X-axis being the principal longer horizontal axis of the apparatus. In the embodiment shown, a single X-axis track 32 is supported at either end on bearing shafts and brackets 34a (left) and 34b (right). The Y-axis is the principal shorter horizontal axis of the embodiment as shown. Stepping motors are used in these embodiments under the control of the computer or other control apparatus (as described below). A portion of one motor mount 33 for the X-axis motion motor is visible in this figure. The Z-axis in this embodiment is the orthogonal vertical axis perpendicular to the plane of FIG. 1.

In preferred embodiments, flexible electronic leads and tubing (both gas and liquid supply conduits) would be shown in this figure leading from movable arm 30 to appropriate fluid reservoirs or electronic control equipment. These leads and conduits are not shown in FIG. 1 for the sake of clarity, but are described later with respect to specific portions of the apparatus. The supply conduits are desirably sufficiently long and flexible so as to withstand the rigors of frequent use. They will originate from different pumps and desirably will be bound together. The various supply conduits pass through a flexible wire carrier 35 to the left side of X-axis track 32, then through another wire carrier 36 which is at the top of the X-axis track to conduct all supply conduits to movable arm 30 and Z head 70.

Figure 2:
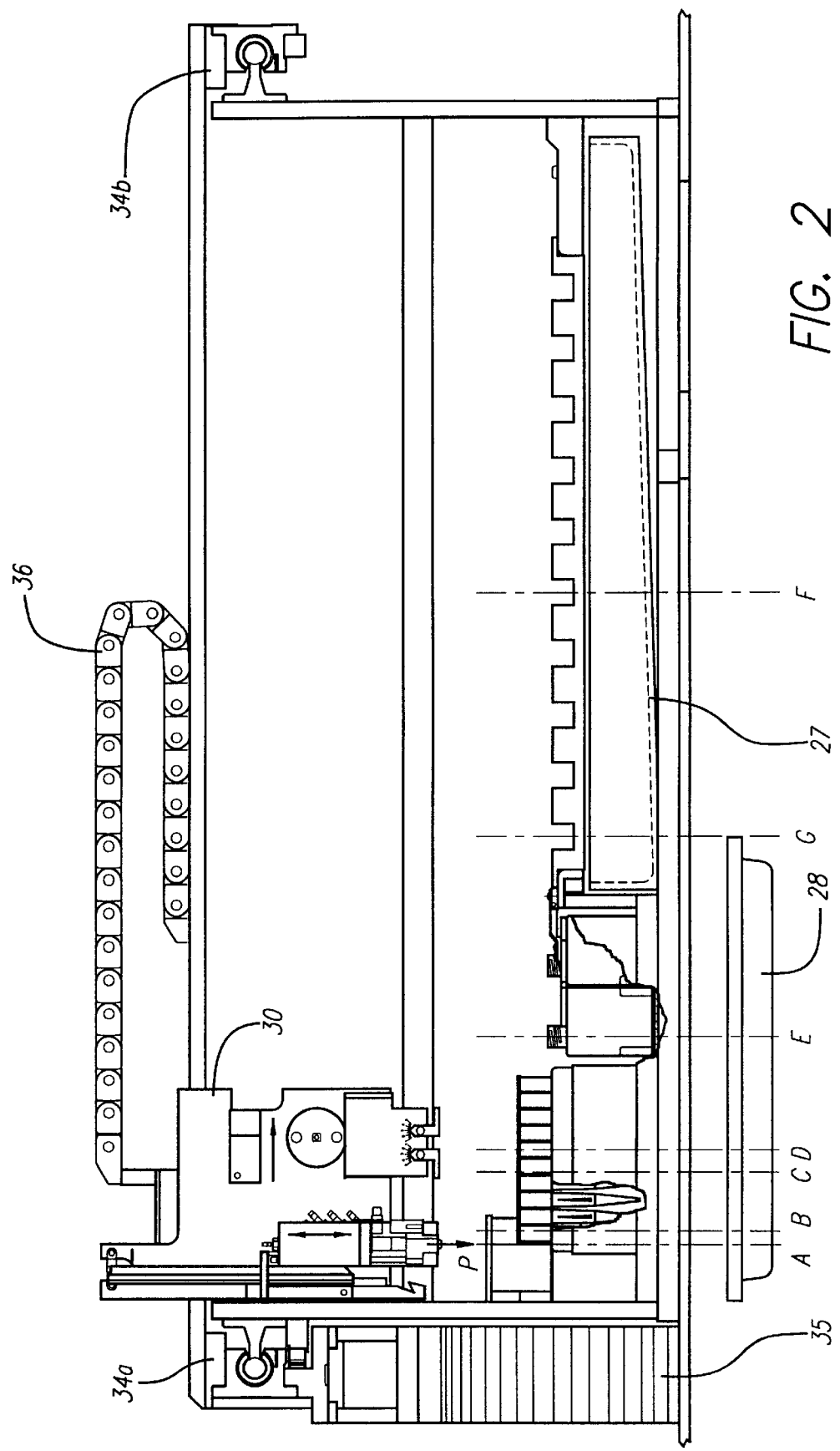
FIG. 2 is a front horizontal elevation of an embodiment as depicted generally in FIG. 1, showing seven separate representative locations (by thick dashed lines A, B, C, D, E, F & G) for the operational movable arm of the apparatus.

The embodiment 10 of FIG. 1 is also shown in FIG. 2. In this front horizontal elevation of the embodiment of the invention, movable arm 30 is shown in its home position, to which the arm returns when not otherwise engaged. The home position is desirably selected to minimize interference with other operations, such as the insertion of microscope slides or disposable pipette tips into the cabinet-like interior of framework 20. FIG. 2 includes seven thick dashed lines (A, B, C, D, E, F & G) along with the X-axis indicating seven different positions for movable arm 30 (the home position plus six representative operational positions). A 'P' arrow line on movable arm 30 points to the dashed lines to indicates the current locations in the figures. The following table lists the positions and the functions implemented at each position, including moistening the optional O-ring:

TABLE 1

| Position | Function | Figure # |
|---|---|---|
| A | movable arm home position | 2 |
| B | moisten reagent tip head and O-ring | 3 |
| C | eject pipette tip | 8 |
| D | engage pipette tip | 5 |
| E | take up reagent solution from vial | 6 |
| F | wash and blow slide | 4 |
| G | dispense reagent solution to slide | 7 |

Figure 3:
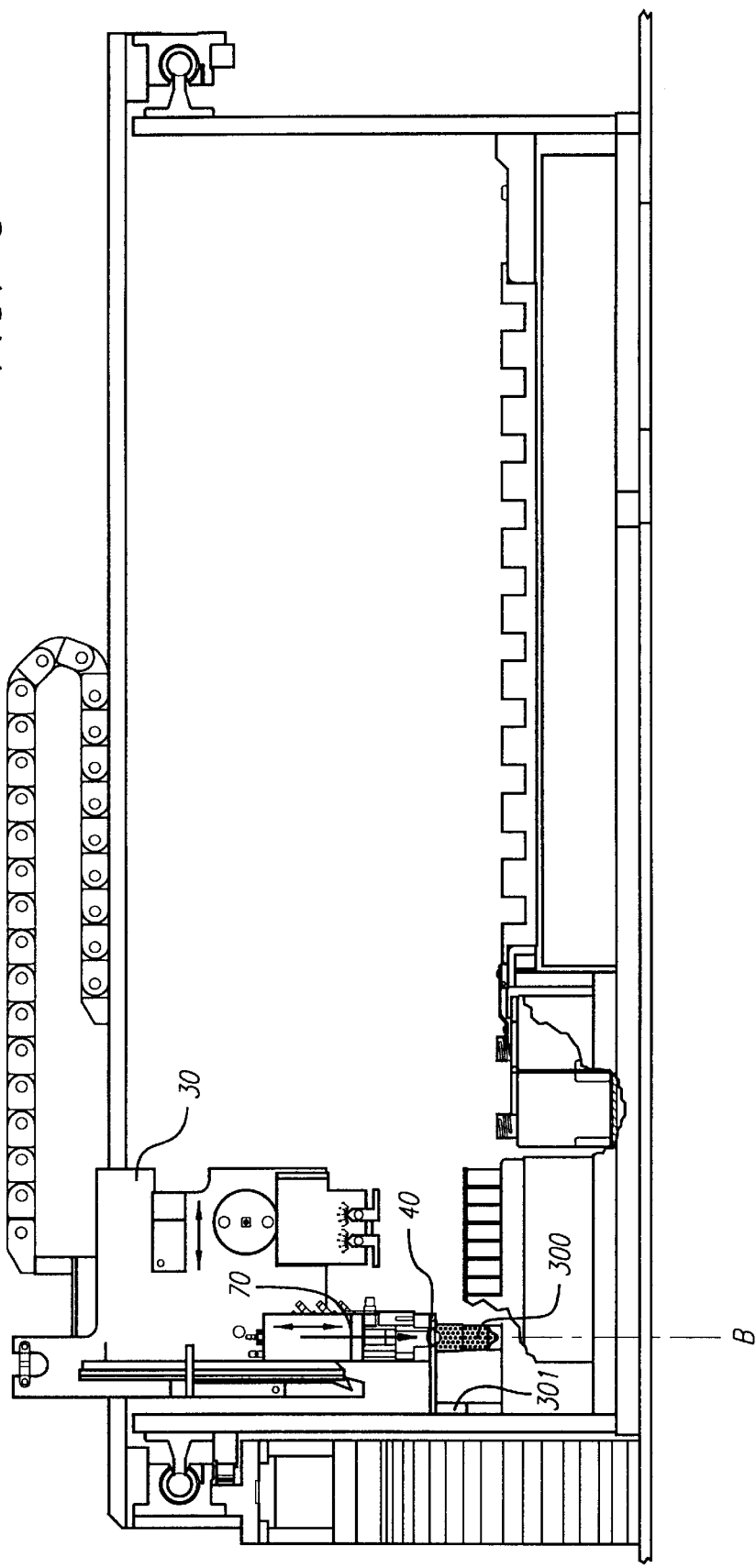
FIG. 3 is a front horizontal elevation of an embodiment as depicted generally in FIG. 2, showing an optional embodiment in which A reagent tip head and optional O-ring are moistened in an optional sponge cup.

In FIG. 3, movable arm 30 is shown at a location where the reagent tip head 40 located on Z head 70 is inside an optional sponge cup 300 suspended from optional sponge cup support 301. Experience has shown that in certain embodiments an optional O-ring 43 in the reagent tip head 40 (see FIG. 10) can be useful to retain and seal a pipette tip or other device onto reagent tip head 40. If such an O-ring 43 is employed, it can be difficult to pick up and retain pipette tips if the O-ring 43 is dry. In these embodiments, either after the reagent tip head 40 has selected a predetermined number of application tips or after a predetermined delay between selections (whichever comes first), the Z head 70 on movable arm 30 can be instructed to move to a position above any interfering part of the apparatus and then move to the position where the reagent tip head 40 is directly above the sponge cup 300 (position B). Then the reagent tip head 40 moves downwardly and inserts into the sponge cup 300, and is submerged into the sponge. The sponge is supplied with water so that the reagent tip head 40 and O-ring 43 will be moistened. The water supply in the sponge cup 300 can be automatically refilled. For example, each time the apparatus is started, the movable arm 30 can be instructed to move the wash tip 41 (see FIG. 10) on Z head 70 to the sponge cup position, and to pump sufficient water from the water reservoir through the water tubing and wash tip into the sponge cup.

Alternatively, the instruction set for controlling the movement of the Z head 70 can be programmed to ensure that the reagent tip head 40 is pressed onto the pipette tip 90 with sufficient force so as to form a tight seal therebetween, minimizing the risk that the tip will be lost inadvertently during the operation of the apparatus. In such embodiments, O-ring 43, sponge cup 300, sponge cup support 301 and the O-ring fitting groove in reagent tip head 40 (see FIG. 10A) may be eliminated. Similarly, the operating station and function depicted in FIG. 3 and Table 1 will be unnecessary.

Figure 4:
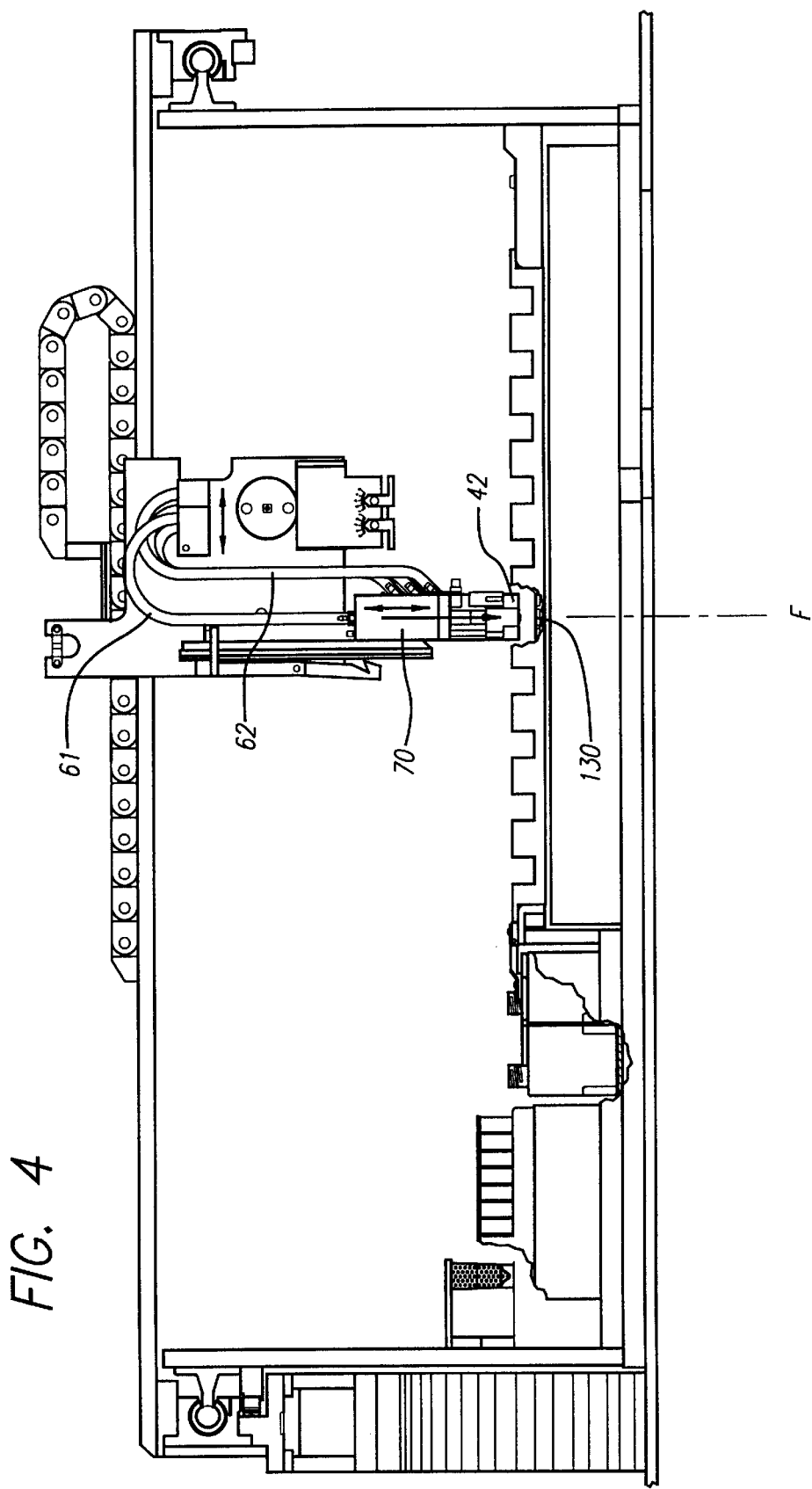
FIG. 4 is a front horizontal elevation of an embodiment as depicted generally in FIG. 2, showing the movable arm at position 'F', wherein the wash tip and blow tip are lowered to proximate the upper surface of a slide for performing wash and blow processing steps.

FIG. 4 is a detailed view of how the wash tip 41 and the blow tip 42 (as shown in greater detail in FIG. 10) operate in the invention. In FIG. 4, wash tip 41 (not shown in this figure) and blow tip 42 are integrated into Z head 70. When initiating a wash and blow operation, Z head 70 on movable arm 30 is moved upward so that Z head 70 is above any interfering part of the apparatus, then movable arm 30 is moved to an appropriate location while Z head is in the raised position. When Z head 70 reaches the appropriate location above a pre-selected microscope slide (position F), Z head 70 is again lowered to position wash tip 41 and blow tip 42 at an appropriate height above the selected microscope slide (as shown). In a preferred embodiment, wash tip 41 and blow tip 42 are positioned at one end (e.g. the front end) of microscope slide 130 and a buffer or wash liquid, supplied through liquid supply conduit 62 (not visible in this figure), flows out from wash tip 41. The Z head 70 is moved in a single pass to the rear of microscope slide 130. If desired, the blow operation can then be carried out on the same slide by supplying pressurized gas through an gas supply conduit to blow tip 42. The Z head 70 is then moved back to the front position of microscope slide 130 while keeping the gas stream from blow tip 42 in motion. However, it is also possible, and preferred in some embodiments to move wash tip 41 and blow tip 42 to a second microscope slide for the addition of buffer, so that the buffer added to the first microscope slide can remain on the slide for a pre-selected period of time prior to removal. After the buffer has been added to a pre-selected number of slides, wash tip 41 and blow tip 42 on Z head 70 are returned to the first slide of the group and the blow operation can commence.

Figure 9A:
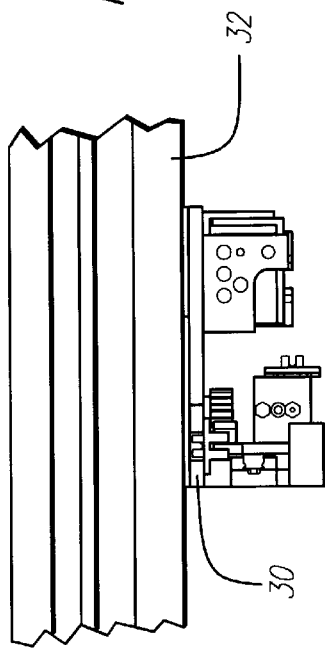
FIG. 9 depicts multiple views including front horizontal elevation, side horizontal elevation, and top plan view of the movable arm and Z head of an embodiment as depicted generally in FIG. 1.
Figure 9C:
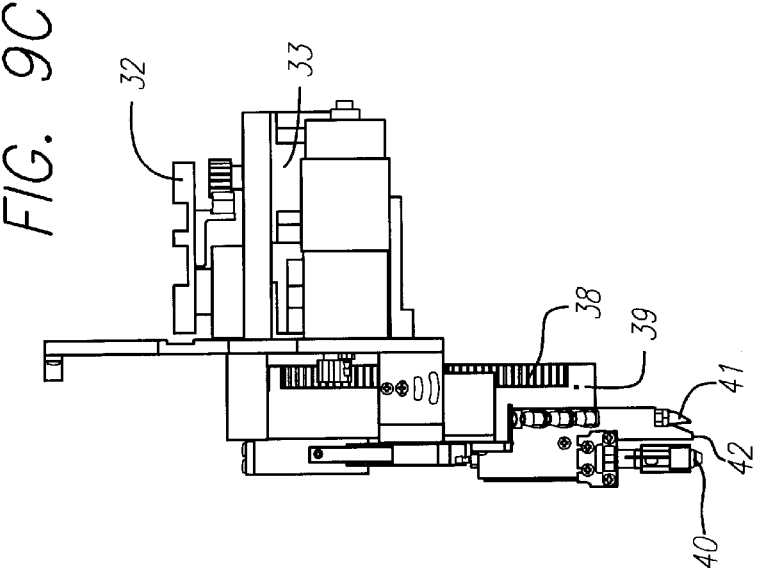
Figure 9B:
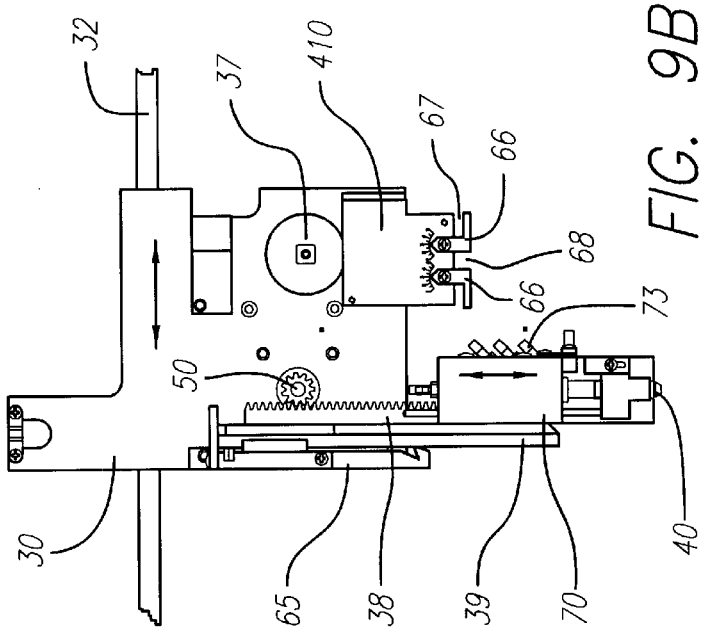

As shown in FIGS. 9 and 10, alternative embodiments of the configuration of wash tip 41 can also be employed. In the embodiment of FIG. 10 wash tip 41 is provided with a bevel (therein depicted as approximately 30°) so that the surface tension of the (typically) aqueous liquid ordinarily dispensed through the tip will prevent the formation of a depending drop of liquid which could loosen from the tip and contaminate a slide while the Z head 70 traverses the apparatus.

Figure 5:
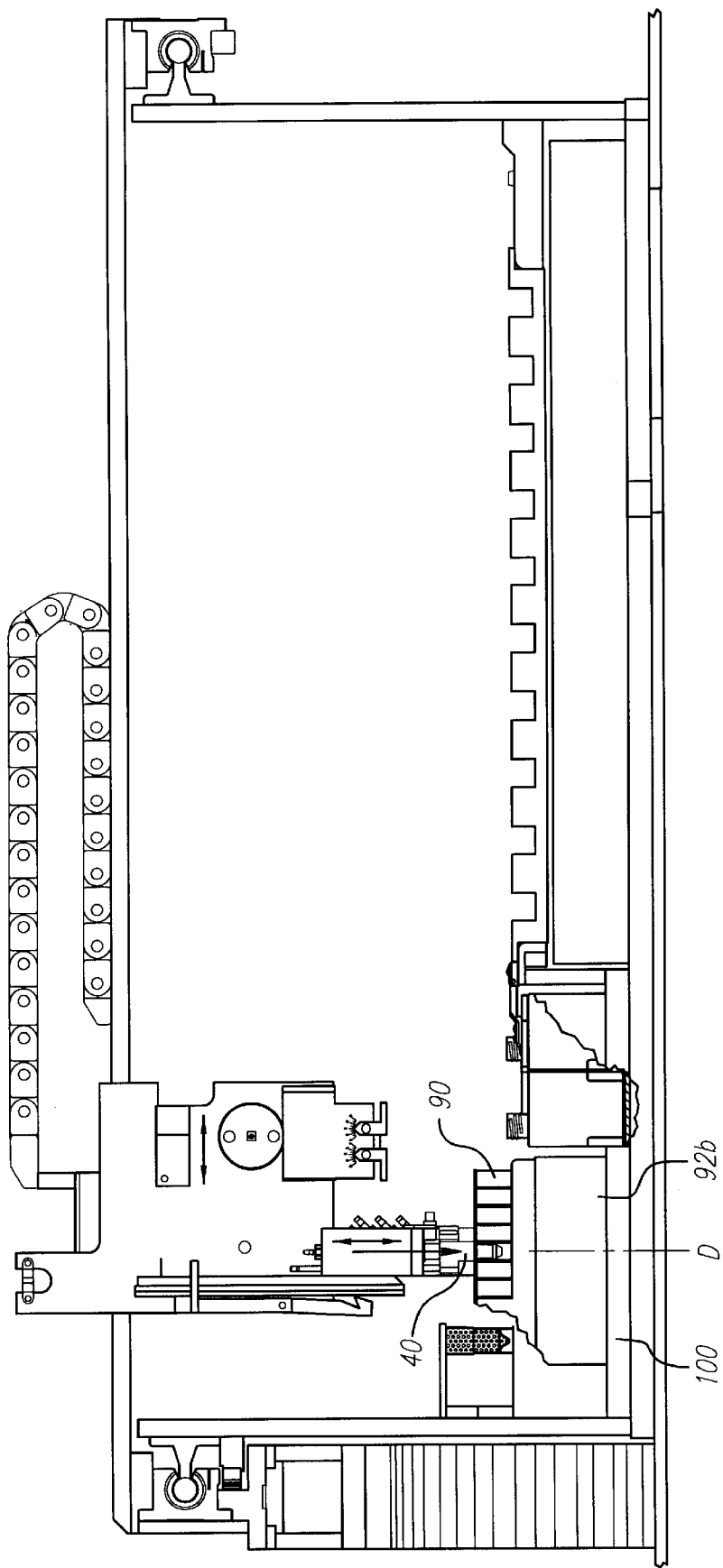
FIG. 5 is a front horizontal elevation of an embodiment as depicted generally in FIG. 2, showing the movable arm at position 'D', wherein the reagent tip head is lowered to engage a pipette tip.

FIG. 5 is a front view of an embodiment shown generally in FIGS. 1–4, wherein the movable arm is in position 'D'. After the wash and blow operations, the apparatus will ordinarily select a pipette tip. The movable arm 30 will be directed to a location such that reagent tip head 40 is directly above and pointing to pipette tip 90 in pipette rack 92*a* or 92*b* positioned onto pipette tip holder 100. The descending Z head 70 presses reagent tip head 40 into pipette tip 90 (here a disposable pipette tip), where the pipette tip 90 is retained on reagent tip head 40 by a press fit in the same manner in which tips are now retained on hand-operated pipettes.

Figure 6:
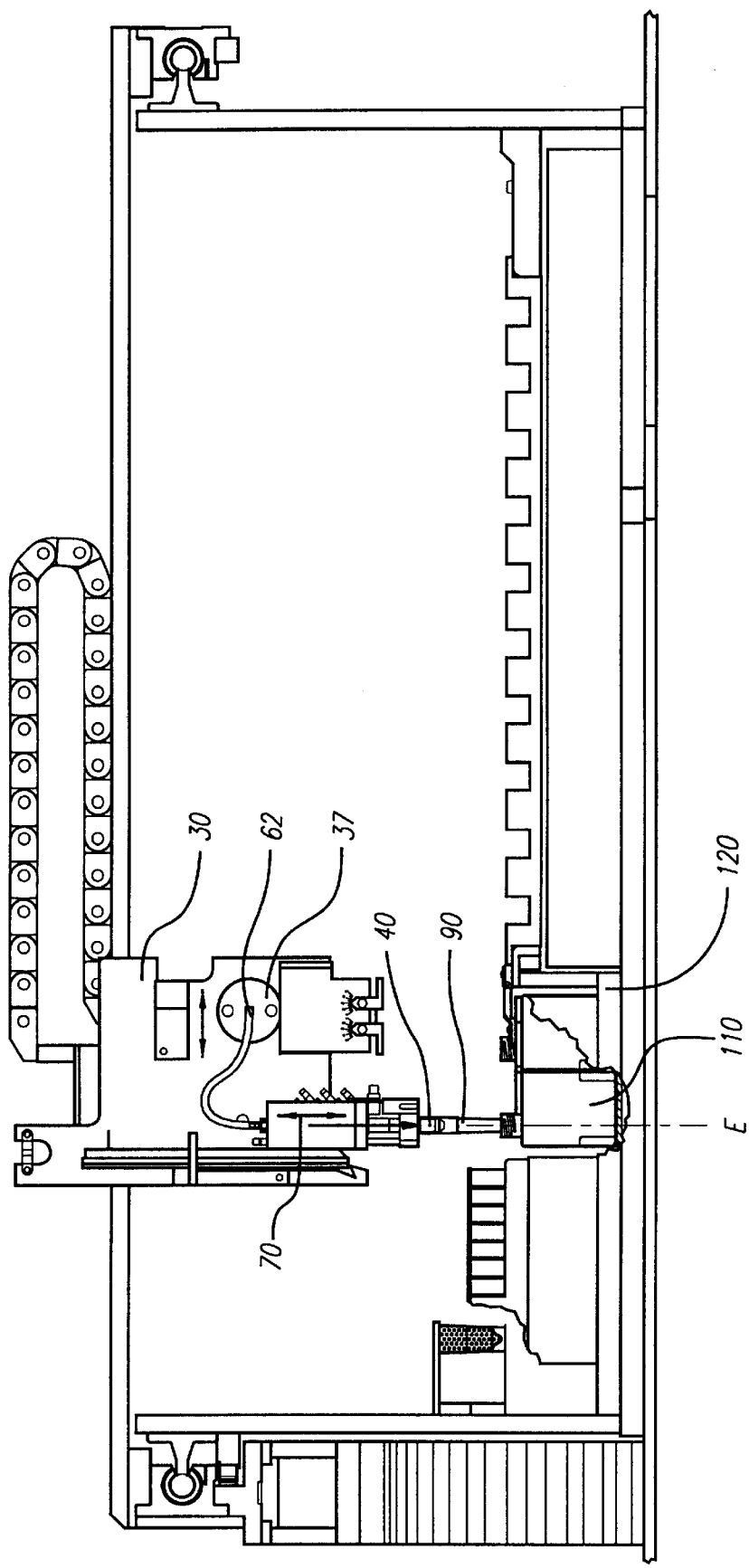
FIG. 6 is a front horizontal elevation of an embodiment as depicted generally in FIG. 2, showing the movable arm at position 'E', wherein the reagent tip head with a pipette tip engaged is moved to a reagent vial, and the tip lowered to the reagent vial to load the reagent.

Z head 70 is then raised and movable arm 30 relocated to position 'E' (as detailed in FIG. 6). Then pipette tip 90 mounted on reagent tip head 40 is lowered into a reagent vial 110 which is held in a predetermined location by reagent vial holder 120. By supplying negative pressure through pipette tip 90, a supply of reagent is drawn into pipette tip 90 for application to microscope slides. A measured volume of reagent can be withdrawn by a precise metering pump 37, which is driven by stepping motors to supply negative air pressure to reagent tip head 40 (i.e., withdrawing air through reagent tip head 40). The application concept of a metering pump used herein is that the liquid located in the supply conduit 62 will act as a piston for withdrawing a specific volume of gas and thus drawing up a specific volume of reagent into pipette tip 90. According to experience and a well-defined conversion table (volume vs. number of steps), the accuracy of the volume can be controlled as appropriate.

Figure 7:
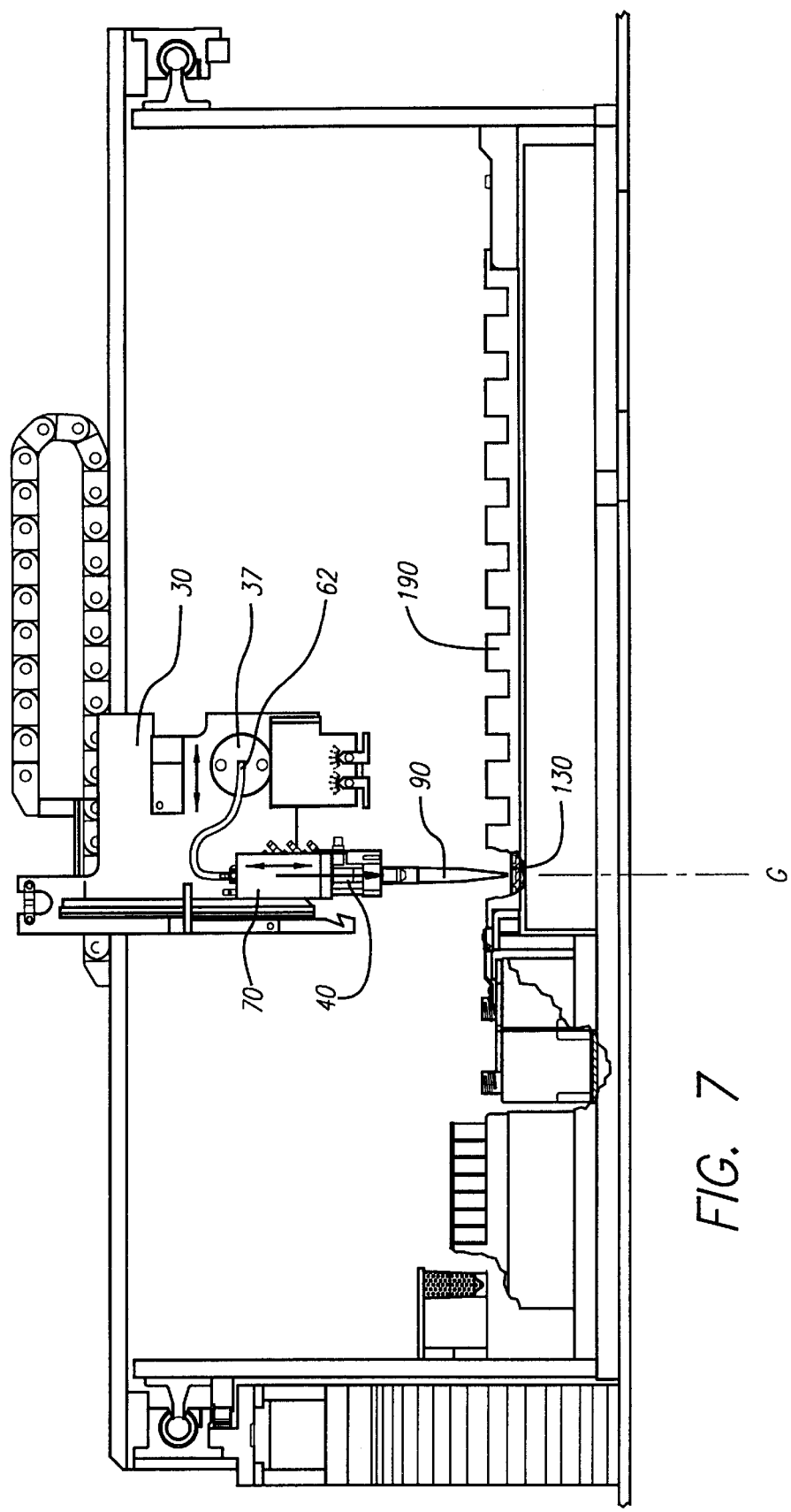
FIG. 7 is a front horizontal elevation of an embodiment as depicted generally in FIG. 2, showing the movable arm at position 'G', wherein the Z head is positioned proximate the microscope slide and the reagent tip head dispenses reagent solution to the slide through the pipette tip.

After a calculated amount of reagent is withdrawn, Z head 70 and pipette tip 90 are then raised as before and moved to position 'G' above a pre-selected microscope slide 130. At the pre-selected position, pipette tip 90 is lowered, and the reagent is applied to the slide. FIG. 7 shows the details of the movable arm 30 and pipette tip 90 at the pre-selected position while applying the reagent to the slide by again using the stepping motor-driven metering pump 37 and the liquid retained in the supply conduit 62 to act as a piston. Reagent can be applied to a single microscope slide 130, or aliquots of the reagent in pipette tip 90 can be applied to different slides according to the calculation of the selected program instructions in the computer control system.

Figure 8:
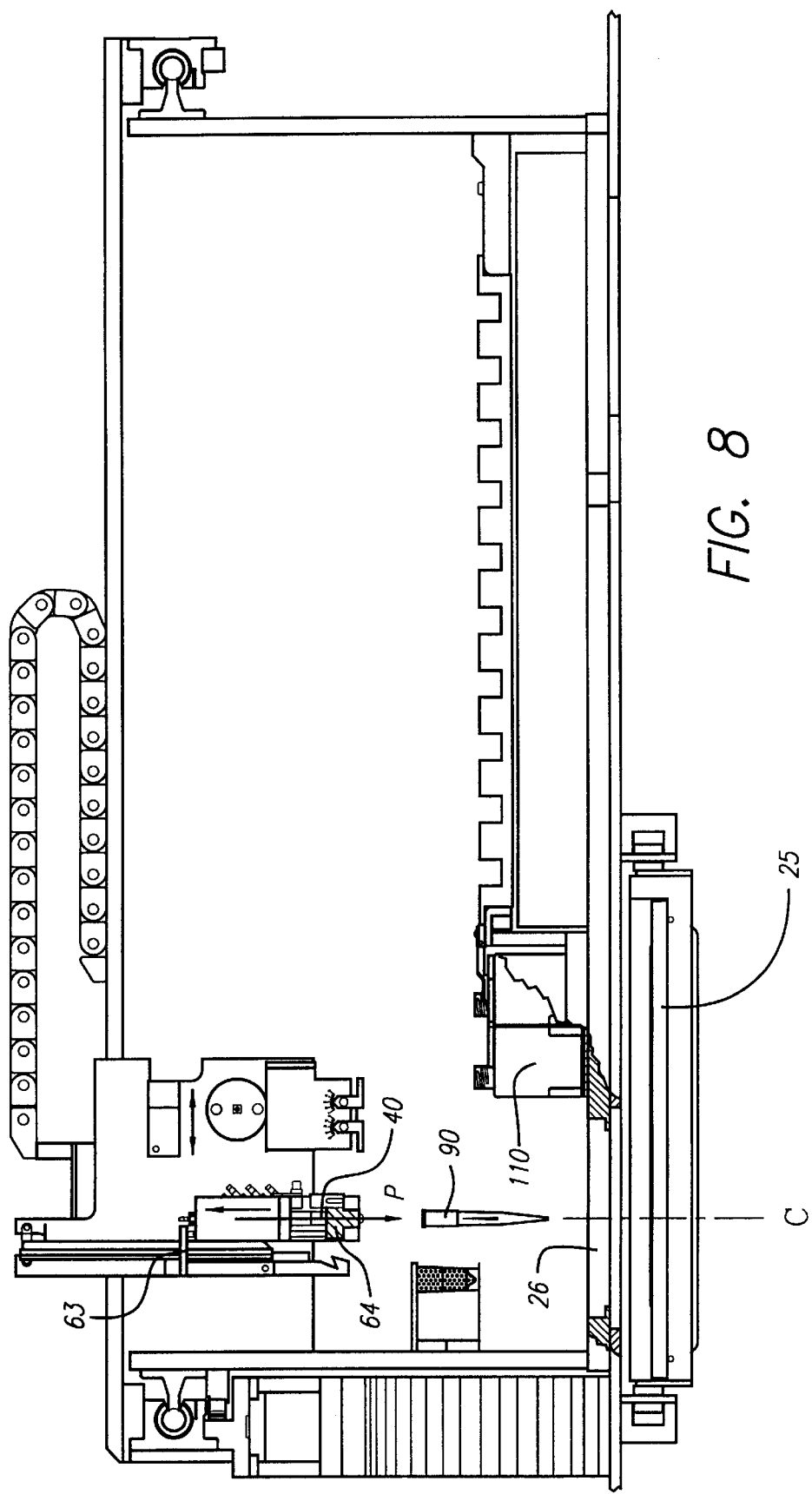
FIG. 8 is a front horizontal elevation of an embodiment as depicted generally in FIG. 2, showing the movable arm at position 'C', wherein the Z head has fully retracted and ejected a pipette tip.

After the reagent is added to the last slide, movable arm 30 is directed to position 'C' above tip disposal orifice 26. A more detailed view is shown in FIG. 8. A tip ejection rod 64 is located on Z head 70, and is adapted to move along the Z-axis of the apparatus. A tip ejection terminal block 63 is located at the side of Z head 70 above tip ejection rod 64. When it is desired to dispose of pipette tip 90, Z head 70 will be raised until the top end of tip ejection rod 64 contacts terminal block 63 installed on Z head 70. Since further motion of tip ejection rod 64 is blocked by terminal block 63, while Z head 70 continues to rise, the lower end of tip ejection rod 64 will press against pipette tip 90 and force the tip off of the end of reagent tip head 40. The pipette tip 90 then drops through tip disposal orifice 26, striking bar 25, and descending into tip disposal bin 27 (not shown) under framework 20 for later removal. The reagent tip head 40 is then lowered to a normal position so that another pipette tip 90 can be mounted on reagent tip head 40.

Figure 18A:
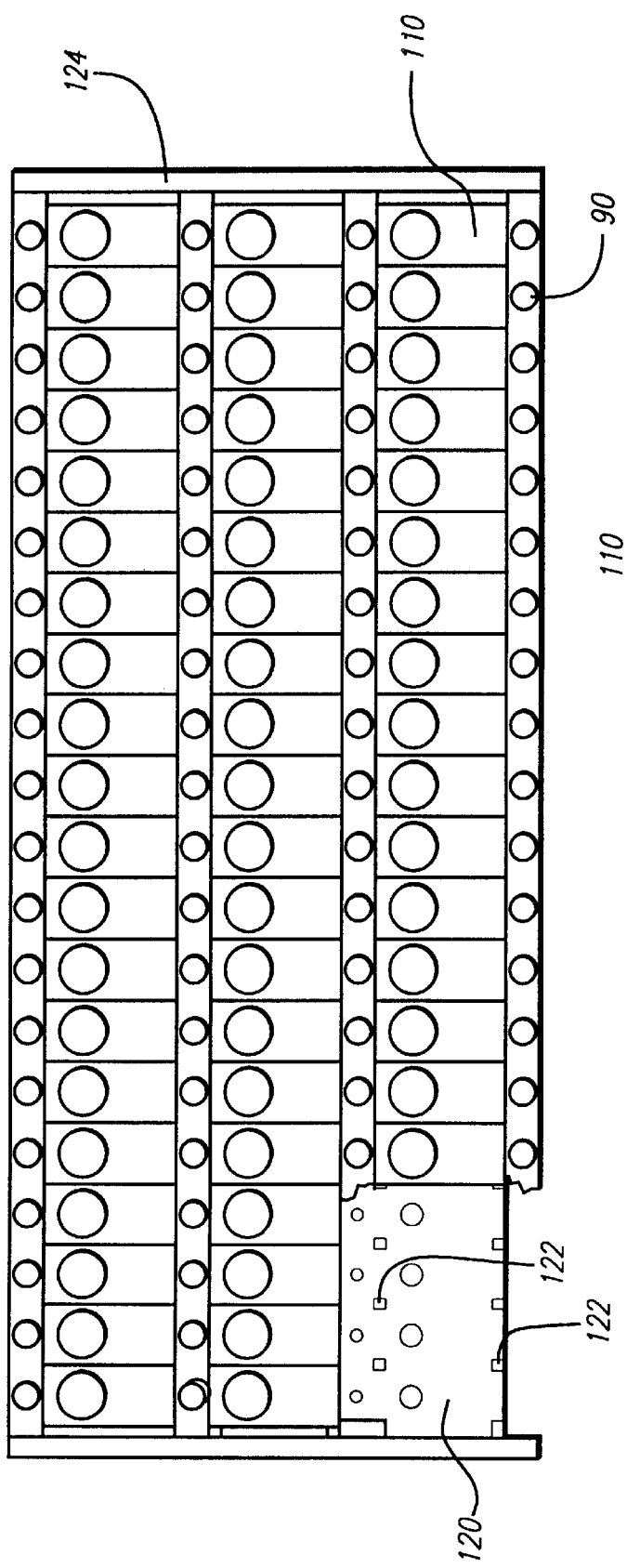
FIG. 18 depicts multiple views including a side horizontal elevation and a top plan view of an alternative embodiment of the pipette tip holder and the reagent vial holder of the present invention.
Figure 18B:
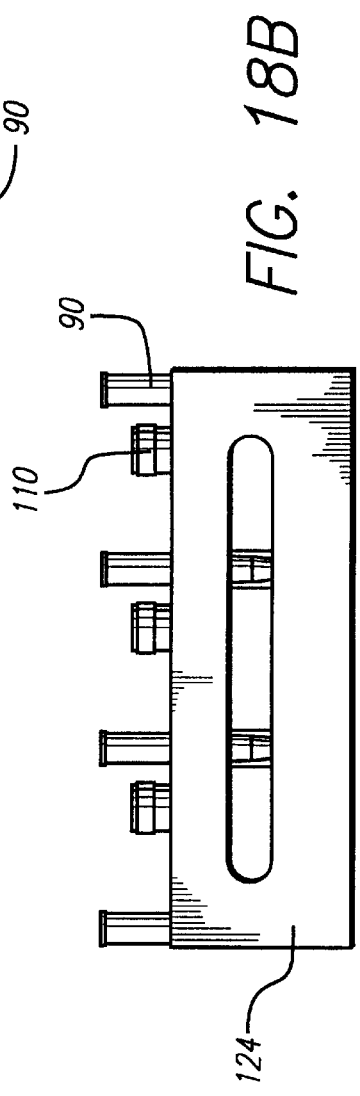

It should be noted that in the embodiments hereinbefore described, the location assigned to pipette tip holder 100 is clearly separate from the location assigned to reagent vial holder 120. As an alternative embodiment (depicted in FIG. 18), these locations could be combined, for example, in an arrangement which stores a single pipette tip 90 in association with each reagent vial 110. In this embodiment, it is contemplated that each time a selected vial 110 is accessed, the reagent tip head 40 would be directed to the associated pipette tip 90 which would then be returned to the holder 100 for reuse after the reagent had been dispensed onto the microscope slide 130. The control means of the apparatus 10 could monitor the volume of reagent remaining in each reagent vial 110, and arrange for disposal and replacement of the vial 110 and pipette tip 90 as appropriate.

One useful design feature of the invention is a highly integrated, multi-functional movable arm 30. FIG. 9 depicts three views of the movable arm 30, showing Z head 70 and reagent tip head 40 without a pipette tip 90 on the head. The Z head 70 is mounted on the Z-axis track 39 and screw lead slide 38. Z head 70 is driven by a Z-axis motor (of which only the output gear 50 is shown in the horizontal front elevation of the figure). A laser bar-code scanner 410 is located on the right side of the Z head 70. There are two scanner shields 66 installed on laser scanner 410. The shields obscure a portion of the laser beam output window 67 and leave the sensor window 68 un-obstructed. By adjusting the shields 66 to a position so that the width of the laser beam after shielding is slightly longer than the length of the bar-code, only one bar-code is read at a time. Since the scanner sensor window 68 is unobstructed, the sensitivity is unchanged. The distance between the laser scanner 410 and the bar-code to be read must be adjusted to insure that the scanner can read the bar-code uniformly. Above the laser scanner 410, is a metering pump 37 which drives the reagent tip head 40 to withdraw and dispense reagent solutions. The means to drive the metering pump can be, e.g., a two-phase stepping motor, desirably with approximately 1.8° of rotation per pulse. A Z head latch 65 is installed on the left side of movable arm 30. When the apparatus 10 is shipped, the Z head latch 65 locks to the Z-axis track 39. The latch will release when Z head 70 returns to its home position. The gas and liquid supply conduits and connection leads are not shown in the drawing, so that the major parts can be seen more clearly. The movable arm 30 is mounted on the X-axis track 32 and can be directed linearly along the track under the direction of a computer or other means of control.

FIG. 10 provides a more detailed view of the reagent tip head 40 on Z head 70. In the figure, the reagent tip head 40 is depicted at the lower right side of Z head 70. In the embodiment shown, reagent tip head 40 has three different diameters at different cross-sections, namely: A segment 40a that is sufficiently large to act as a stop when press-fitting pipette tip 90 onto tip head 40; an intermediate section 40b that acts as the press-fit location for pipette tip 90; and a smaller-diameter segment 40c at the end of tip head 40. In certain embodiments, an O-ring 43 is installed and inserted into a groove on the smaller-diameter segment 40c. When utilized, the outer diameter of O-ring 43 is selected so that when pipette tip 90 is pressed onto tip head 40, O-ring 43 will seal the space between tip head 40 and pipette tip 90. The O-ring 43 thus engaged helps to eliminate leakage and increase the friction fit of pipette tip 90, thereby securing the retention of pipette tip 90; a feature of benefit where pipette tip 90 may suffer from some degree of shape distortion. As disclosed above, alternatively the instruction set for controlling the movement of the Z head 70 can be programmed to ensure that the reagent tip head 40 is pressed onto the pipette tip 90 with sufficient force so as to form a tight seal and thus minimize the risk that the tip will be lost inadvertently during the operation of the apparatus.

FIG. 11 shows a series of views of wash tip 41 and blow tip 42. On the left of the figure is a sectional view of Z head 70, depicting three vertical channels in this embodiment. The left channel is provided for wash tip 41, the middle channel is for blow tip 42, and the right channel is for reagent tip head 40. The reagent tip head 40 is not shown in the figure, for clarity of presentation of the remaining features. The hollow interior of blow tip 42 is not limited to the specific shape shown, although certain advantages are obtained for aspects of this interior shape and slit shape as described below. In general, the hollow interior 77 of the blow tip 42 can vary significantly in shape as long as sufficient access is provided for easy flow of gas into interior space 77 so that pressure differentials do not build up and cause differential exit of gas through exit slot 79. Exit slot 79 is generally located on the bottom-most surface of blow tip 42 and is preferably a linear exit slit having a length substantially equal to the width of a standard microscope slide of the type selected for use in a particular operation. As there are different sizes of microscope slides, different wash and blow tips can be prepared for the dimensions of each such microscope slide. As shown in the sectional view C of FIG. 11, access 78 between hollow interior space 77 and exit slit 79 is preferably provided so that gas leaving slit 79 exits at an angle to the vertical. By providing exit slit 79 at a slight angle and moving Z head 70 in a direction toward the obtuse angle formed between the gas wall and the microscope slide 130, the removal of water or buffer from slide 130 is facilitated.

At the right side of FIG. 11 is a sectional view of a liquid distribution embodiment of the invention. There is portrayed a main vertically-oriented hollow located at the center of the embodiment. An opening 76 shown at the top of the embodiment is used during the manufacture of the device, and will ordinarily be blocked after the installation is completed. However, opening 76 can also be used as an inlet for an extra liquid supply. Wash tip 41 will be installed at the lower end of the embodiment, and is not shown in the figure. On the side wall of the embodiment, there is a row of liquid solution inlet connectors. This array of parallel channels provides a path for the incoming liquid solution to be distributed to the main hollow portion, which can then flow down to wash tip 41. The advantage of this design is that by using individual supply lines to deliver different solutions, interference and cross-contamination will be minimized. One important feature of this embodiment is the angle between inlet cavities 73 and main cavity 76. A major consideration for the orientation of this angle is to minimize liquid flow resistance and to prevent liquids from flowing into adjacent hollows or supply lines, which could cause cross-contamination. In addition, using individual pumps for each liquid solution is a simple and effective way to control liquid solution supply individually; no extra valves are needed and no backflow or cross-contamination will occur.

Figure 12:
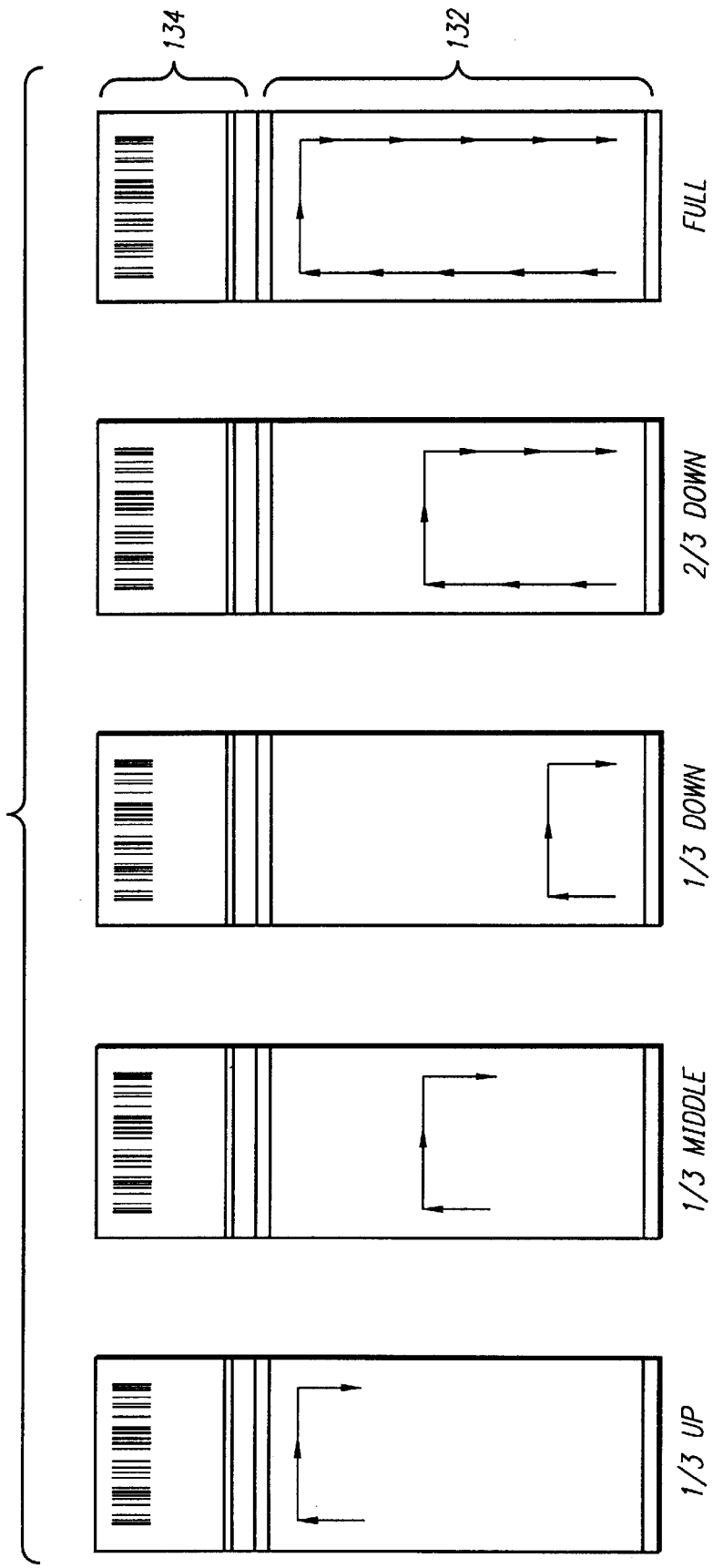
FIG. 12 is a top plan view of a number of microscope slides showing the specimen location and bar-code regions of the slide as well as exemplary reagent dispensing patterns for the method of the invention for applying reagents to slides.
Figure 13A:
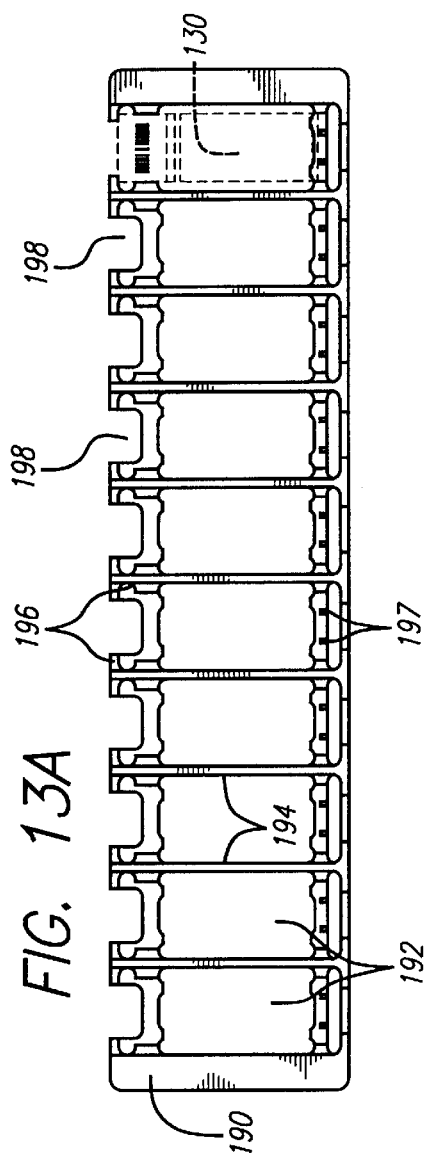
FIG. 13 depicts multiple views including elevations, plan views and perspective views of an individual microscope slide tray used in an embodiment as depicted generally in FIG. 1.
Figure 13B:
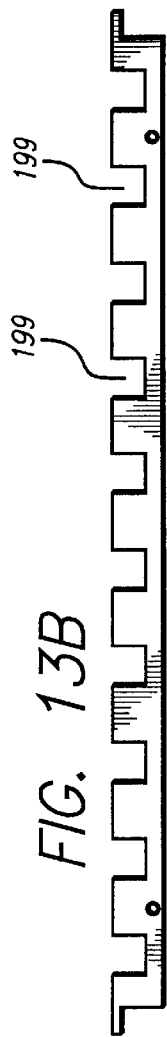
Figure 13C:
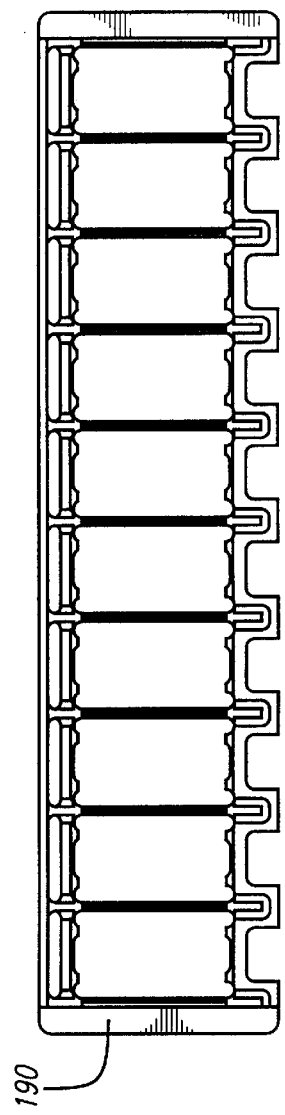
Figure 13D:
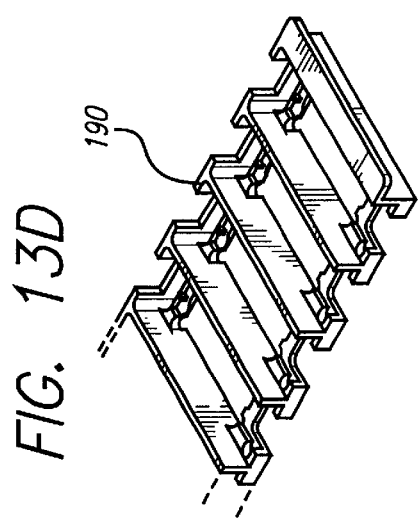
Figure 13E:
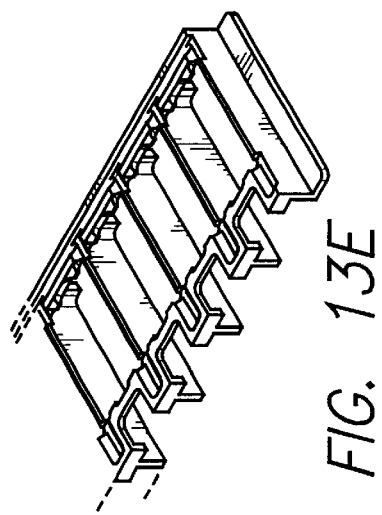

FIG. 12 shows several typical reagent dispensing patterns on a microscope slide 130. Most slides will have a specimen region 132 and a second region 134 for including information on the slide. Because of the nature of the procedure for mounting specimens on slides, a specimen can be present at any location within region 132. As previously discussed, the thin film of buffer that will be present when a reagent is dispensed onto the slide assists in ensuring that adequate reagent is applied to the specimen, regardless of where the specimen is located or the reagent is applied. However, in a preferred embodiment of the apparatus, the reagent is dispensed in a pattern, rather than a single location, so that the distance that a reagent must diffuse through the liquid film is reduced. Several typical reagent dispensing patterns are shown in FIG. 12, although other patterns will prove equally useful.

Furthermore, the ⅓ and ⅔ patterns depicted in FIG. 12 restrict dispensed reagent to a portion of region 132, in order to conserve reagents if a specimen occupies only a limited portion of the region. This can prove valuable where the reagents are expensive, such as, e.g., nucleic acid probes. To take full advantage of this conservation strategy, it may also be desirable to restrict the dispensed reagent from spreading beyond the application area, for example by the use of a fluid barrier. Special slides are available commercially which include pre-established fluid barriers, or the user can establish such barriers by creating a border around the specimen with a hydrophobic material, such as a marker (PAP) pen, also available commercially.

FIG. 13 shows multiple views of a tray 190 intended to hold microscope slides. Tray 190 is formed into a series of individual wells 192 for microscope slides; the location of a single microscope slide 130 is shown by a dotted line in the right-most well of the plain view in FIG. 13. The design of the well fits both 1"×3" U.S. standard and 26×76 mm European standard microscope slides. Individual side walls 194 separate each well 192 from its adjacent wells to prevent accidental contact of liquid, such as might occur during a washing operation, and to prevent contamination between adjacent microscope slides. The open bottom of each well 192 allows buffer to drain through the bottom of tray 190 where it will be disposed of, typically in a drain bin 27 as shown in FIG. 2. The open bottom of the well 192 will also permit the use of projections on the baseplate 22 to raise the slide 130 above the tray 190, so that the edges of the slide 130 in the region where reagent is applied are not in contact with the tray 190, thus precluding a capillary wicking of reagent or other solution and possible cross-contamination of the slide. The side walls 194, retaining tabs 196 and bracing feet 197 closely and accurately retain microscope slides placed into the individual wells. A gap 198 is present at one end of well 192 to allow easy grasping of an individual microscope slide 130 between thumb and forefinger for insertion into and removal from tray 190. As discussed previously, the blow tip 42, wash tip 41 and reagent tip head 40 are integrated onto Z head 70 as one embodiment. Thus, when performing a blow operation, the blow tip head 42 is located very close to the surface of slide 130 which is set into the slide tray 190, and the reagent tip head 40 at the same height is positioned just in front of blow tip 42. A row of head openings 199 at the front wall is designed to provide a space for reagent tip head 40 when blow tip 42 moves to the rear end of the slide 130. Removable trays 190 are designed for ease of operation by allowing a user to place microscope slides 130 in a loading tray 190 outside the apparatus 10 in which the staining operations will occur. Another advantage of allowing trays 190 to be removed from the slide tray holder is to simplify the process of cleaning and other maintenance work. The tray 190 also will be adapted to fit precisely into other elements at the appropriate location on base plate 22.

Figure 14A:
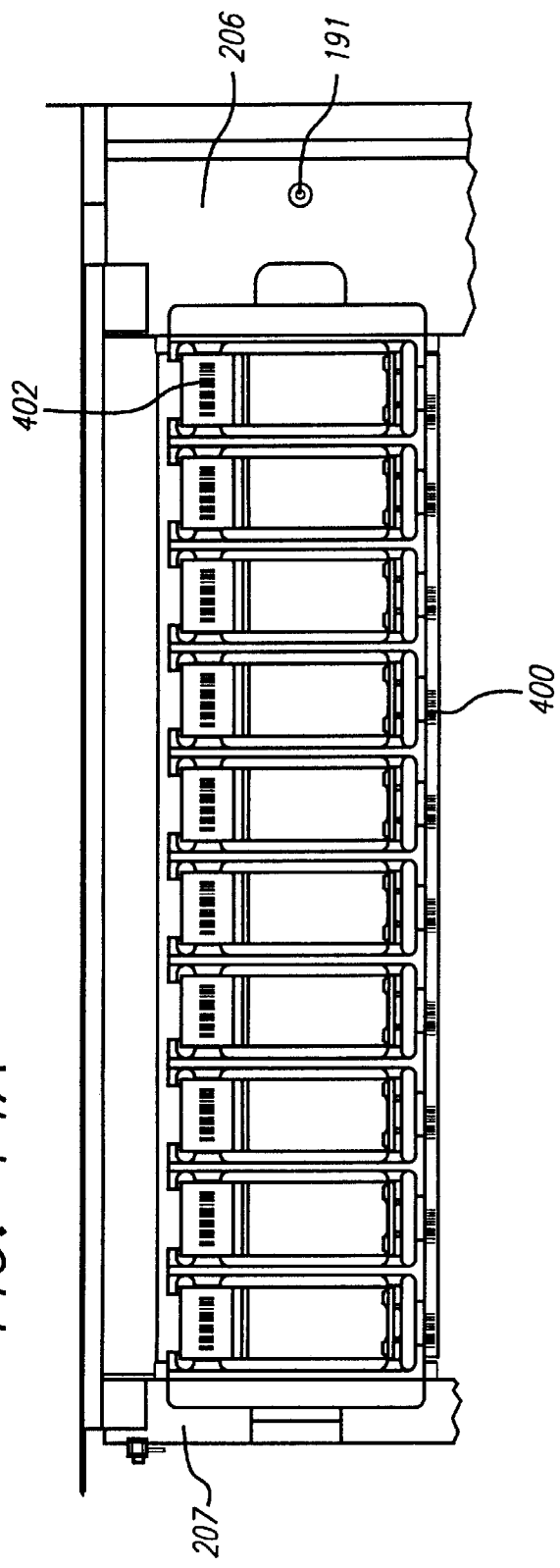
FIG. 14 depicts multiple views including a front horizontal elevation and a top plan view of the slide tray holder, tray and the associated locking structure.
Figure 14B:
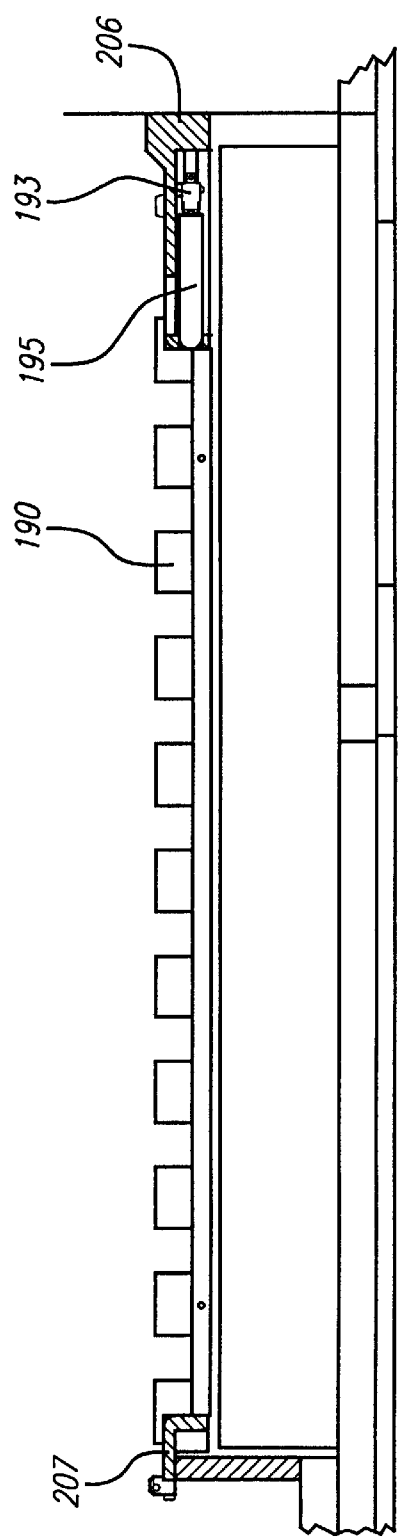

As shown in FIG. 14, right tray support 206 and left tray support 207, which are installed on the baseplate 22, contain four slide trays 190 in a row, each of which is capable of containing 10 slides for a total of 40 microscope slides in a predetermined array. FIG. 14 shows how a tray 190 is set onto tray supports 206/207. In certain embodiments, on right tray support 206, there are four sliding rods 195 installed horizontally, facing and against the outside wall on the right side of the tray 190. The another end of sliding rod 195 (right side) is linked with a micro lever switch which is in turn electrically connected to a in-position light 191. The sliding rod 195 can freely move left or right. A detailed view is shown in FIG. 14. When there is no tray on the tray support, the sliding rod 195 is at the left-most position, so that switch 193 is 'off' and the light 191 is likewise off. When a tray 190 is fully inserted into tray support 206 and at the right position, the right side wall of the tray 190 pushes sliding rod 195 to the right, pressing the micro lever switch to its 'on' position, then activating the light 191. The light 191 then indicates that the tray 190 is now in the correct position and ready for staining. Another function for sliding rods 195 is to 'soft lock' the trays 190 and prevent them from moving when the apparatus 10 is in operation. In using such a sensing mechanism, care should be taken to prevent contamination from spilled liquids or particulates which could obscure the light path from light 191, thereby falsely indicating the presence of a loaded rack.

FIG. 14 also depicts the slide location bar-code 400 which can be presented on strips associated with the baseplate 22, the tray supports 206/207 or with the microscope slide tray 190. This bar-code 400 will aid the control means in associating a selected slide 130 with the proper reagent vial 110 and staining protocol. While the relative positions of microscope slides 130 in the present embodiment can be established by scanning only three strips of bar-code 400, as a practical matter there is no appreciable loss of efficiency in utilizing a bar-code to identify the location of every slide in the apparatus.

As shown in FIG. 1, reagent vial holder 120, located at the left side of slide tray support 207 is designed to hold up to 40 reagent vials and can accept reagent vials having a wide range of capacities, typically from 5 mL to 25 mL. Alternatively, a vial holder block (not shown) having appropriate dimensions could be utilized in place of the depicted vials. Such a block could include a bar-code and present a smaller vial, such as a screw-cap vial commonly used to contain small volumes of expensive reagents, in proper orientation for access by the reagent tip head 40. Such a holder block can thus extend the useful volume range as low as is practical, typically as low as 0.1 mL, a range commonly associated with nucleic acid reagents.

A detailed view of one embodiment of reagent vial holder 120 is shown in FIG. 15. The total of 40 reagent vials are divided into two columns with 20 vials in each. The left column of reagent vial holder 120 contains reagent vials #1 to #20 starting from the upper left corner of reagent vial holder 120 (see FIG. 1) and down to vial #20 in the same column in vial holder 120. The right column of reagent vial holder 120 holds reagent vials #21 to #40. The vial numbers can be engraved right at the position where the reagent vial will be located. These numbers correspond to the specific reagent vial numbers in the programming of the instrument. As shown in the figure, the spacing prongs 122 between two reagent vials (up and down, left and right) are designed to maintain certain spacing between adjacent vials, and accommodate shape/size distortions of the plastic reagent vials 110. In this manner, the reagent vials will be secure in the proper positions. Handles 124 can be installed at both ends of reagent vial holder 120 to simplify manipulation.

As can be seen in FIG. 15, a reagent location indicator 403 is mounted on left slide tray support 207. Hinges are used to allow the location indicator 403 to be repositioned when loading the reagent vials 110 onto vial holder 120; and the location indicator 403 can be returned to cover the tops of the reagent vials after loading. This reagent location indicator 403 resembles a 'fish bone,' with a 'spine' in the middle and total of 38 'fins' evenly spaced on both side of the 'spine.' A bar-code and a human readable number is printed on each 'fin' to indicate the reagent vial number. When in working position, the indicator 403 is in a horizontal orientation laying on the tops of the reagent vials 110. The 'spine' is then located at the center divider of two columns of the reagent vials; each fin is positioned between two adjacent reagent vials in a column, and the bar-codes on the "fins" are 'inserted' between the bar-codes on the reagent vials 110.

As also shown in FIG. 15, the reagent vial 110 will also be configured so as to provide a region 112 for the bar-code label in a horizontal orientation on the upper surface of the vial. In this manner, the reagent vial information can be readily accessed at the same time as the location information from indicator 403. The use of the bar-code information from the various bar-codes will be covered in detail below.

One desirable feature of the present apparatus is that the design which minimizes the risk of cross-contamination between slides, reagents, and liquid solutions enables the use of the present apparatus for aspects of specimen preparation and slide processing heretofore unavailable in an automated slide staining device. For example, FIG. 16 shows various components used in the supply of gas and wash liquids to Z head 70. An gas compressor 170 provides gas through flexible conduit 61 to movable arm 30, Z head 70 and ultimately to blow tip 42. A computer controlled switch controls gas pump on and off to control the gas supply. Buffer or other wash solutions are supplied by individual pulse metering pumps. The volume of liquid is controlled by the number of pulses sent to the metering pump. Pump 173 is for DI water, pump 174 is for Buffer solution and pump 175 is used for pumping dewaxing solutions. Different liquid solution are pumped from individual reservoirs through individual supply tubing conduits 62, movable arm 30, Z head 70, and finally to the common wash tip 41. The material used for supply conduit tubing must be selected individually for specific liquid solutions. For example, the tubing used for dewaxing solutions should be resistant to organic solvents and detergents, for example Viton-type tubing. Thus, the present apparatus enables the inclusion of a dewaxing slide preparation step in the automated protocols implemented by the control system. This is a feature previously unavailable in apparatus which process microscope slides in a horizontal orientation. Representative of protocols useful in such slide preparation protocols are the methods disclosed in PCT Publication WO 95/24498 and in U.S. Pat. No. 5,578,452, the entire contents of which is incorporated herein by this reference. In this manner, the use of volatile organic solvents in dewaxing operations can be minimized, and the apparatus can perform such operations without requiring special ventilation.

Figure 17:
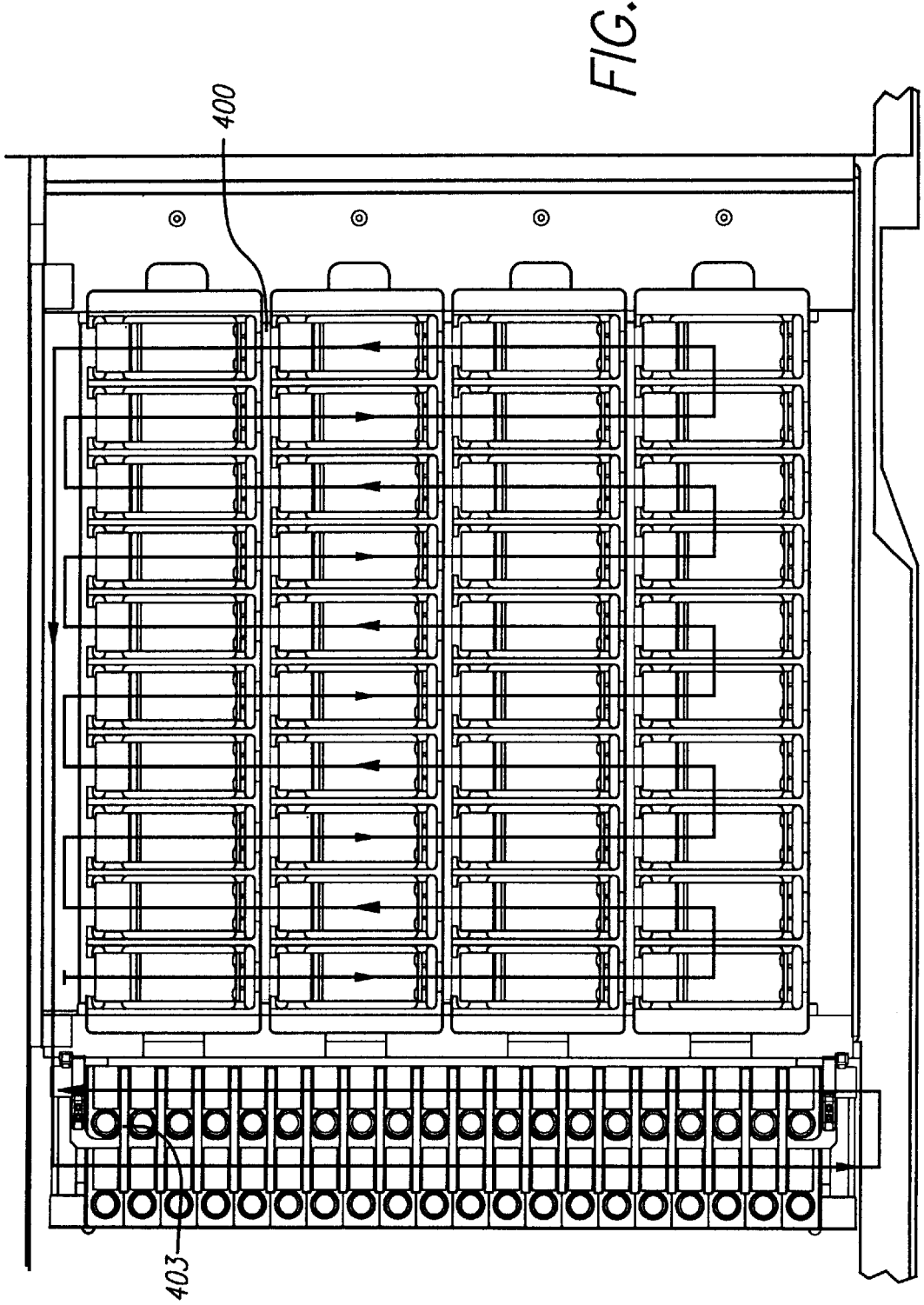
FIG. 17 is a top plan view of one trail that the bar-code scanner could trace to read the bar-code on reagent vials and microscope slides. The location indicator codes are also depicted.

FIG. 17 depicts a typical trail that the laser bar-code scanner 410 will trace when reading the bar-codes on both microscope slides 130 and reagent vials 110. A batch processing method is generally used in bar-code reading in the present invention. Rather than reading the bar-codes and acting on the information individually, the laser scanner 410 scans the bar-codes by batch in order to increase processing speed. In a typical pattern, laser scanner 410 begins scanning at the left most slide 130 in tray #1 (top row). The scanner 410 on the movable arm 30 moves vertically down to the bottom row (tray #4), the scanner reading the bar-codes 402 on slide #1, #11, #21 and #31, and each location indicator bar-code 400 which is in the same column as well. The information can be saved in laser scanner 410 as it scans, then transferred to the computer, e.g. via a RS232 serial port, using a protocol compatible for both. The most commonly used protocol in this regard is 7 bit data, 1 bit stop and even parity check. Movable arm 30 then moves one slide left, where laser scanner 410 is aiming at the microscope slides in the next column (#2, #12, #22 and #32). For this pass, movable arm 30 moves from bottom to top, while laser scanner 410 reads the bar-codes 400/402 in reversed order. After reaching the top row of slide tray 190, again the information can be transmitted to the computer. These steps are repeated until all the slide and location bar-codes are read. As discussed previously, slide location indicator 400 (with associated bar-code) can be installed on each slide tray (optionally except row #1 or #4). When reading the bar-codes 402 on the slides, the laser scanner 410 also reads the bar-code on indicator 400 between the two bar-codes on the slides. Thus, slide location information is 'inserted' during the reading process. If any bar-code is not properly read, or missing, the computer is capable of identifying which slide is "missing" and a menu on the computer screen informs the user to manually input the missing information or to re-run the scanning procedure. As soon as the microscope slide scanning is completed, movable arm 30 moves laser scanner 410 to the reagent vials 110 and the same steps can be used to read all desired information on the reagent vials 110 and reagent vial location indicators 403. One benefit of this batch processing strategy is that the apparatus can process trays of slides in a manner which completes the prescribed processing on a single tray 190, and then signal the user to remove the tray and replace it with a fresh tray, without interrupting the processing of the remaining trays. In this manner, the apparatus can be utilized continuously with a minimum of intervention by the user.

It will be apparent to one of ordinary skill that many of the specific elements shown in the figures and described above can be replaced by other elements that perform the same function. For example, the X, Y, and Z tracks can be replaced by a single robotics arm. Additionally, it will be understood that the specific tracks, motors and other individual parts can be replaced by other parts of equivalent function. In a preferred embodiment of the invention, the X, Y, and Z tracks are purchased as commercially available sliding tracks. The X-axis and Z-axis motions are supplied by a linear motion rail assembly and linear motion guide (Part Nos. LWES 20C1 R690 H/LCR and SEBS 9AUU-I-155 respectively from Specialty Motions, Inc.) and stepping motors (Part No. PK266-02A for the X-axis and PK243-01AA for the Z-axis, both supplied by Automation Motor Controls). The Y-axis shaft system is a linear bearing rail assembly (Part No. SRA-8-PD-21-55 also supplied by Specialty Motions); power along the Y-axis was supplied by the same stepping motor used for the X-axis. Electrical connections, tubing, compressed gas distribution systems, liquid distribution systems from a central reservoir, and many other components such as holders for a standard pipette tip rack or for reagent containers are commercially available from a variety of suppliers. Thus, the apparatus of the invention can be prepared from readily available commercial parts assembled in the manner described, with a minimum number of specialized manufacturing techniques. Since the Z head 70 is not readily available, it will typically be manufactured for a particular apparatus as shown or in a similar manner to provide the features that are described in the specification above.

The composition of the components from which various parts are manufactured can vary widely, but components through which reagents pass or which contact potentially corrosive reagent or wash solutions are typically prepared from stainless steel or inert plastics to prevent corrosion. The Z head 70 with its integrated tips and other features is typically formed from a moldable plastic (such as a polyacrylate) and can be prepared by a molding process, a plastic-shaping process, or some combination thereof depending on the individual shape intended to be utilized. Parts that are subject to wear, such as the stem 38 and reagent tip head 40 of Z head 70 are typically prepared from a hard plastic or other material that will resist wear.

The present apparatus is typically operated under the control of a computer or other programmable control device. In the simplest applications, where only a single type of automated staining well be performed repeatedly, it is possible to provide either a hard-wired controller or a non-programmable electronic controller, such as a computer operating under instructions from read-only memory. In preferred embodiments, however, a programmable controller or computer is used so that the operation of the apparatus can be varied. Software will generally be provided with the computer so that the user does not need to provide instructions for individual motions, but merely selects appropriate motions from a menu.

In an 'open' format, for a typical operation, a user would be asked to select the location and volume of the reagents, the location of the slides being treated, and the length of time for various steps such as incubation times; all other operations can be carried out by the pre-programmed instruction set in the memory of the computer, which will control actual movement of the movable arm to the appropriate locations and activation of the various gas and liquid control systems.

In a 'closed' format, bar-code technology can be used to supply instructions to the apparatus. The apparatus reads bar-codes associated with both the reagent vials 110 and the slides 130; thereafter the computer is able to determine all parameters needed to carry out the most appropriate pre-programmed instruction set in the memory of the computer to control the apparatus in the processing procedures for microscope slide staining. Compared with the 'open' format, less user input is required, thus reducing the opportunities for introduction of error.

The preparation of pre-programmed instruction sets to carry out the various operations of the present apparatus is a matter well within the routine skill of a computer programmer, when provided with the disclosure of the present invention. As noted previously, it is considered desirable to provide an instruction set which will ensure that the reagent tip head 40 is pressed onto the pipette tip 90 with sufficient force so as to form a tight seal therebetween, minimizing the risk that the tip will be lost inadvertently during the operation of the apparatus. In addition, it has been found desirable to control movement of the Z head 70 in the "Z" axis by calculating motion from the current position (i.e. the relative movement) rather than from the home position (i.e. the absolute movement). This feature will avoid lost steps, provide more accurate positioning and help to reduce "dead volume" (i.e. less reagent remaining at the bottom of a reagent vial. It is also possible to provide within the instruction set provisions for recovery from a loss of pipette tip during a staining routine, as well as machine calibration.

One desirable step in the method that is used in the automated apparatus of the invention involves blowing excess reagent or buffer off the surface of the slide 130. A preferred embodiment of the tip used in this blowing operation is shown in FIG. 11, although other tips having slits for exit of gas to provide a wall of gas can also be used. By adjusting the gas pressure, height of the exit slit above the microscope slide, and rate of movement of the slit, the extent to which liquid is removed from the slide can be varied. The amount of liquid present in the thin film on the microscope slide's upper surface is quite small, typically from 2 to 25 microliters, more generally from 3 to 20, and preferably from 5 to 10. The area to be covered is generally approximately 15 cm$^2$, providing a typical volume per surface area of approximately 0.13 to 1.7 microliter/cm$^2$. However, it is difficult to determine the actual volume being used, since the operation of blowing liquid off the top surface of a slide causes liquid to adhere to other portions of the microscope slide, making measurement of the remaining liquid difficult. Thus, the volume of liquid present on the slide upper surface at the end of a blow operation is best determined empirically. The maximum permissible volume is determined by the stain being used and its concentration at the reagent application stage, since these factors affect the final concentration of the stain or other reagent on the surface of the slide. Historical procedures developed for slide preparation are generally described in terms of a particular reagent concentration, incubation time, and temperature. Accordingly, it is desirable to provide a minimum volume of liquid on the slide in order to avoid having to change the concentration of reagents from the standard used in the industry. By adhering to this guideline, it is possible to use commercially available, ready-prepared stain solutions as reagents.

On the other hand, too little liquid on a slide can cause problems in reagent spreading, particularly due to evaporation. Since buffer is added to a slide prior to addition of reagent and motion of the moveable arm to pick up pipette tips and reagents takes time, the buffer must remain on the slide until reagent is added, which further may not occur until after the preparation of other slides. Since it is more efficient to prepare multiple slides at one time, rather than to require repeated movements of the movable arm and repeated pickup motions form the various heads, a typical minimum volume of buffer would be that amount which is sufficient to allow preparation of at least four slides without requiring removal of a given tip.

The gas pressure, height of the head above the slide and rate of motion of the head for control of the liquid film can all be selected by the user or by the manufacturer of the apparatus. Generally, the same gas pressure will be used at all times so as to remove this variable from consideration. Thus, only the height of the head and the rate of motion will typically be varied. The higher the head above the slide, the less liquid will be removed. The faster the head is passed across the slide for a given height, the less liquid will be removed.

For a standard 1 inch by 3 inch microscope slide surface area and a blow tip having the configuration shown in FIG. 11, an gas pressure of 7 psi (0.5 cm/sec), a height of 0.07 inch (2 mm) above the microscope slide surface, and a rate of motion of 3 inch/sec (7.5 cm/sec) provide a preferred buffer film suitable for the staining of four slides at 25° C. and a relative humidity of 60–80%, which is the typical humidity present inside a closed and operating apparatus of the invention.

The wash solutions used in the apparatus of the invention can vary significantly depending on the staining technique being used. A typical wash solution is an aqueous solution of a surfactant and can contain other components present in typical slide preparation of wash solutions, such as buffers.

In preferred embodiments, sufficient surfactant is present to provide a surface tension in a solution equivalent to that present in solutions containing water and the following surfactants at the concentrations listed. Typical surfactants used (with concentrations shown in parenthesis) are TWEEN™ 20 (0.02 to 2% v/v), BRIJ™35 (0.05 TO 3% v/v), and TRITON™ X-100 (0.01 to 1% v/v). Typical buffers used are phosphate buffered saline and TRIS-Cl (each at approximate pH 7.6). For conciseness of language, the specification and claims often refer to water as the wash fluid or the fluid being removed at a particular step. It will be apparent that this "water" can and generally is an aqueous solution of buffer and surfactant or of some staining reagent.

It will be apparent that the apparatus of the invention can be used in any staining technique that can be carried out manually and that there are no limitations placed on the invention by the staining technique.

The apparatus of the invention can contain a number of further components designed for ease of operation. For example, drain trays with exit conduits to waste reservoirs can be located either individually under components of the apparatus or a single drain tray and collection system can be provided for the entire interior space of the apparatus frame. In a typical apparatus, the framework is a form of a cabinet with an interior space in which all operations take place. A closeable access port (e.g., a door) can be provided to allow user access to maintain the various consumable components into the interior cabinet space. A transparent door can be provided to prevent accidental spraying of liquid (as during a blowing operation) into the room in which the apparatus is located, while allowing the user of the apparatus to visually verify proper operation. Other optional features that can be included on the apparatus include devices intended to ensure level operation, to protect against electric shock, to verify that an appropriate tip has been selected and properly placed on the tip head, or to optically scan slides in a microscope slide tray or other container for microscope slides so that a user is not required to enter information into the computer. Such information could be provided, for example, by a standard bar-code attached to an individual microscope slide or the component. Multiple reagent containers can be provided so that different staining operations can be carried out under the control of the bar-code system and the computer and its pre-programmed software.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

REFERENCES

U.S. Patent Documents

| U.S. Pat. No. | Issue Date | Inventors | Class |
| --- | --- | --- | --- |
| 3,853,092 | 12/1974 | Amos et al. | 118/56 |
| 4,004,550 | 01/1977 | White et al. | 118/314 |
| 4,013,038 | 03/1977 | Rogers et al. | 118/5 |
| 4,304,700 | 07/1977 | Basset et al. | 118/2 |
| 4,043,292 | 08/1971 | Rogers et al. | 118/5 |
| 4,088,797 | 05/1978 | Johnson | 427/2 |
| 4,200,056 | 04/1980 | Johnson | 118/401 |
| 4,985,206 | 01/1991 | Bowman et al. | 422/99 |
| 5,009,185 | 04/1991 | Stokes et al. | 118/52 |
| 5,180,606 | 01/1993 | Stokes et al. | 427/2 |
| 5,231,029 | 07/1993 | Wootton et al. | 435/289 |
| 5,439,649 | 08/1995 | Tseung et al. | 422/99 |

Other Publications

"Ventana 320 Automated immunostaining system," Marketing brochure for Ventana Medical System, Inc., Tucson, Ariz. (date unknown).

"Jung Histostainer Ig Automated Immunostainer," Marketing brochure for Leica Instrument GmbH, (date unknown).

What is claimed is:

1. An automatic apparatus for staining a microscope slide comprising:
   a supporting framework;
   at least one arm moveable in three dimensions attached to said framework;
   means for moving said arm;
   at least one hollow tip head located on said arm;
   at least one reagent tip head located on said hollow tip head further comprising means for releasably engaging a pipette tip by a pre-selected movement of said arm;
   means for alternatively supplying positive or negative gas pressure to said reagent tip head to withdraw or dispense volumes of liquid onto a microscope slide via said reagent tip head and pipette tip;
   at least one wash tip located on said hollow tip head comprising means for selectively dispensing a plurality of liquids onto the microscope slide;
   at least one blow tip located on said hollow tip head comprising means for selectively dispensing a gas onto the microscope slide via an exit slit substantially equal in length to the width of the slide;
   at least one pipette tip holder at a predetermined location on said framework adapted for holding a plurality of pipette tips adapted to be releasably attached to said reagent tip head;
   at least one reagent vial holder at a second predetermined location on said framework adapted for holding a plurality of reagent vials;
   at least one microscope slide holder at a third predetermined location on said framework, said microscope slide holder being adapted to releasably contain the microscope slide; and
   control means operatively connected to said means for moving said arm, said means for alternatively supplying positive or negative gas pressure, said means for selectively dispensing a plurality of liquids, said means for selectively dispensing gas and said means for controlling movement of said arm between said predetermined locations, said control means adapted to cause said tip head to engage a pipette tip, to release the pipette tip, to withdraw a reagent from said reagent vial, to dispense said reagent onto said slide via said pipette tip, and to dispense a gas or a liquid onto said slide through said wash tip and said blow tip.

2. The apparatus of claim 1, wherein said supporting framework comprises a cabinet having an interior space and all of said predetermined locations are in said interior space.

3. The apparatus of claim 2, wherein said cabinet has a closeable access port.

4. The apparatus of claim 1, wherein said arm remains in a predetermined location in the absence of power being supplied to said means for moving said arm.

5. The apparatus of claim 1, wherein said arm moves along independent X, Y, and Z axes for independent movement of said tip head in three orthogonal directions.

6. The apparatus of claim 5, wherein said X and Y axes are oriented in the horizontal plane of said apparatus when said apparatus is in its normal operating orientation.

7. The apparatus of claim 1, wherein said apparatus further comprises a plurality of individual liquid pumps in selectable fluid communication with said wash tip via said hollow tip head.

8. The apparatus of claim 1, wherein said means for supplying gas pressure comprises a gas compressor.

9. The apparatus of claim 1, wherein said means for supplying gas pressure is capable of withdrawing or dispensing a predetermined amount of gas through said reagent tip head, said predetermined amount being selectable by said control means, thereby providing precise withdrawing or dispensing of a liquid into or from a pipette tip engaged with said reagent tip head.

10. The apparatus of claim 9, wherein said means for supplying gas pressure comprises a moveable piston that controls the movement of a liquid in a liquid supply conduit between a liquid reservoir and said reagent tip head.

11. The apparatus of claim 1, wherein each of said wash tip and said blow tip are individually integrated into said hollow tip head.

12. The apparatus of claim 1, wherein said pipette tip holder is adapted to retain at least one rack of disposable tips, whereby said tips are retained by said holder as an array of pipette tips at a predetermined location and orientation for access by said tip head.

13. The apparatus of claim 1, wherein further comprising at least one additional reagent vial holder at a fourth predetermined location on said framework.

14. The apparatus of claim 1, wherein said apparatus further comprises a microscope slide tray releasably engaged with said framework and adapted to retain multiple microscope slides in a predetermined array at said third location.

15. The apparatus of claim 14, wherein said tray comprises individual wells for each microscope slide and said wells are partially open on their lower surfaces.

16. The apparatus of claim 1 wherein said hollow tip head further comprises a laser bar-code scanner adapted to read a bar-code.

17. The apparatus of claim 1 wherein the reagent vial holder comprises a reagent vial locator between each reagent vial including a bar-code indicator to indicate the location of each individual reagent vial.

18. The apparatus of claim 15 wherein said microscope slide tray comprises a slide locator bar-code region on the slide tray including a bar-code indicator to indicate the location of each individual microscope slide on the tray.

19. The apparatus of claim 1, wherein said control means comprises a programmable computer system.

20. The apparatus of claim 1, wherein said control means is adapted to cause a gas to be blown through said blow tip at a predetermined time as said blow tip is moved horizontally over said microscope slide.

21. The apparatus of claim 1, wherein said control means is adapted to cause a pipette tip on said reagent tip head to withdraw and hold for transfer a predetermined volume of a reagent from a selected reagent vial, thereafter to cause said reagent tip head to move to a preselected location above a preselected microscope slide in said microscope slide holder, and thereafter to cause said pipette tip to dispense a predetermined volume of said reagent onto said microscope slide in a preselected pattern.

22. The apparatus of claim 1 wherein said control means comprises a plurality of formats for the control of the said apparatus.

23. The apparatus of claim 22 wherein at least one of said formats is a closed format which utilizes bar-code information to supply at least some of the information required for automatically processing microscope slides.

24. The apparatus of claim 22 wherein at least one of said formats is an open format which permits a user of the apparatus to select at least one parameter to supply the information required for processing microscope slides.

\* \* \* \* \*